US006238364B1

(12) United States Patent
Becker

(10) Patent No.: US 6,238,364 B1
(45) Date of Patent: May 29, 2001

(54) LACRIMAL SILICONE STENT WITH VERY LARGE DIAMETER SEGMENT INSERTABLE TRANSNASALLY

(76) Inventor: Bruce B. Becker, 5363 Balboa Blvd., Suite 246, Encino, CA (US) 91313

(*) Notice: Subject to any disclaimer, the term of this patent is extended or adjusted under 35 U.S.C. 154(b) by 0 days.

(21) Appl. No.: 09/500,424

(22) Filed: Feb. 9, 2000

Related U.S. Application Data

(62) Division of application No. 09/018,439, filed on Feb. 4, 1998.

(51) Int. Cl.$^7$ ................................................ A61M 5/00
(52) U.S. Cl. ........................................................ 604/8
(58) Field of Search .............................. 604/8–10, 285, 604/294, 500; 606/108

(56) References Cited

U.S. PATENT DOCUMENTS 3,726,284 * 4/1973 Parker .
5,318,513 * 6/1994 Leib et al. .
5,437,625 * 8/1995 Kurihashi .

* cited by examiner

*Primary Examiner*—Sharon Kennedy
*Assistant Examiner*—Catherine Serke

(74) *Attorney, Agent, or Firm*—Milton M. Field

(57) ABSTRACT

A lacrimal silicone stent has a very large diameter segment with a diameter greater than the largest diameter stent which can be pulled through the canaliculi readily without damaging the canaliculi, a thin central segment, a moderate diameter segment, and a distal segment with a lumen extending partway from its end. A lumen can also be provided in the very large diameter segment to enhance its flexibility. In addition, a lumina may be provided in the moderate diameter segment when it is formed as an extruded tube. Except for the lumina, the stent is solid. The stent may be molded in one piece, but it may also be made of molded and extruded segments which are fused together. To install the stent, according to a first method a sheath is inserted through the lacrimal system from the eye, through a DCR ostium into the nasal cavity. The distal segment is threaded into the sheath which is used to pull the distal segment back through the lacrimal system and out the superior canaliculus and punctum. A probe is inserted through a sidewall of the distal segment into the lumen. The probe is then pushed through the inferior punctum, the inferior canaliculus, the common canaliculus, the lacrimal sac and the DCR ostium into the nasal cavity. The probe is removed, and the stent is then pulled until the very large diameter segment is deployed transnasally through the DCR ostium. According to a second method, the distal segment of the stent is swaged on the probe which is used to feed the distal end of the stent through the sheath and help pull the very large diameter segment transnasally to stent the ostium.

16 Claims, 18 Drawing Sheets

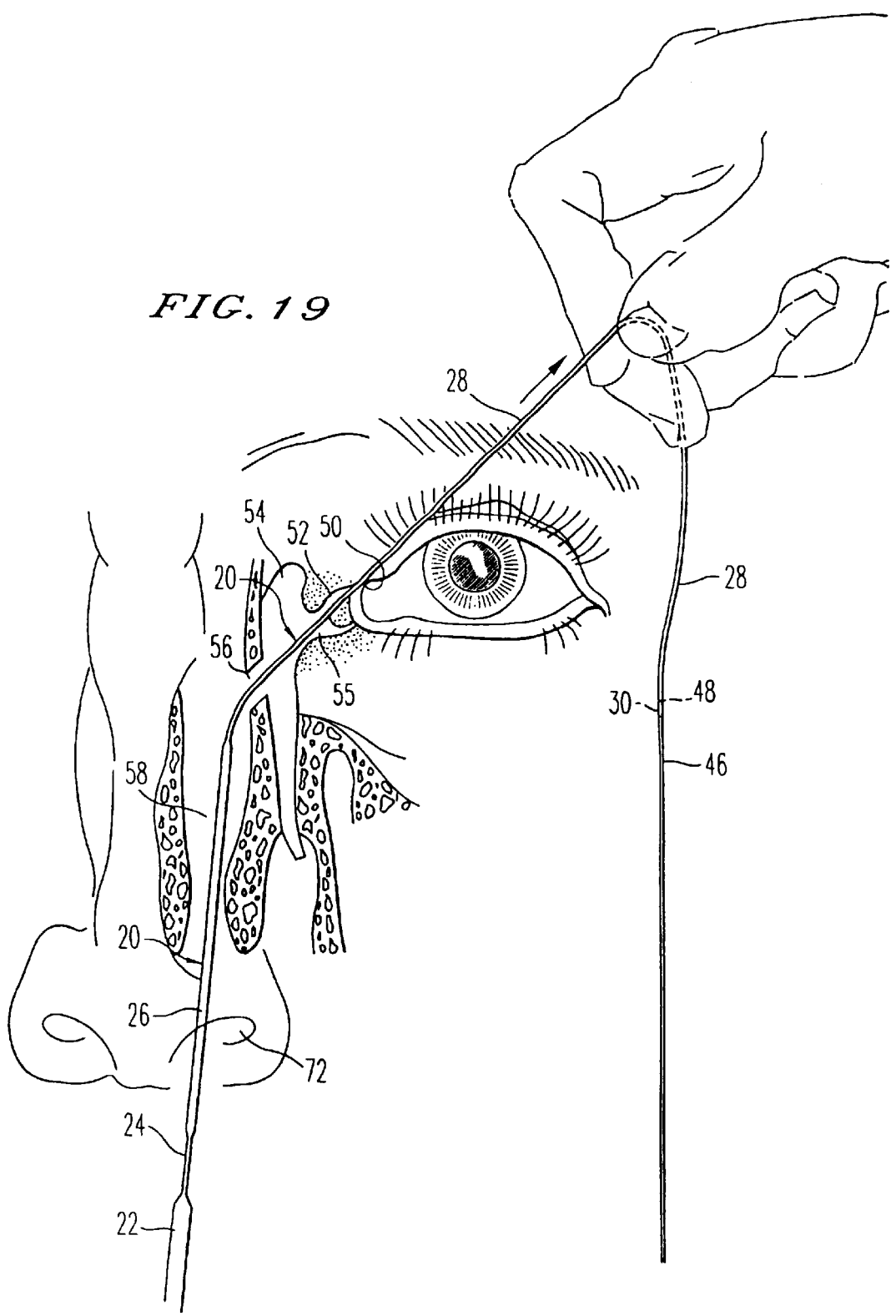

LACRIMAL SILICONE STENT WITH VERY LARGE DIAMETER SEGMENT INSERTABLE TRANSNASALLY

This application is a division of application Ser. No. 09/018,439, filed Feb. 4, 1998.

BACKGROUND OF THE INVENTION

1. Field of the Invention

This invention relates to lacrimal silicone stents and a method of inserting the same, and more particularly, to asymmetric lacrimal silicone stents having a very large diameter segment which is inserted transnasally.

2. Description of the Prior Art

The lacrimal gland produces the aqueous layer of the tear film. The orbital portion of the lacrimal gland is located in the superior temporal orbit. Ductules from the main lacrimal gland pass through the adjacent palpebral lacrimal gland to empty in the superior conjunctival cul-de-sac which is on the posterior surface of the superior upper lid. Accessory lacrimal glands in the upper and lower lids also contribute to tear production.

The tears bathe the eye and then flow into the upper and lower puncta, which are located on the medial upper and lower lid margins. The tears then drain through the superior and inferior canaliculi, common canaliculus, lacrimal sac, and down the nasolacrimal duct into the nose. The nasolacrimal duct can become obstructed either congenitally or as an acquired obstruction in adulthood. When the nasolacrimal duct becomes obstructed, tears can no longer drain from the surface of the eye through the lacrimal system into the nose. The tears therefore well up over the eyes and spill over the lids onto the face. The patient has to constantly dab the eyes with a tissue. In addition, tears stagnate in the lacrimal sac which allows bacteria to multiply. The lacrimal sac then becomes infected (dacryocystitis). Dacryocystitis causes the lacrimal sac to become swollen, red and painful. Pus exudes from the lacrimal sac through the canaliculi onto the eye. This results in purulent material constantly covering the eye. In time, the dacryocystitis does not respond to antibiotics and surgery becomes necessary.

Dacryocystorhinostomy (DCR) is the surgery used to correct nasolacrimal duct obstruction. In a DCR, a new opening (ostium) is created between the lacrimal sac and the nose. This allows tears to flow from the lacrimal sac through the DCR ostium into the nose. An open or incisional DCR requires an incision on the side of the nose. In an open DCR, a large DCR ostium is created by making a 17 mm. plus opening in mucosa and bone. This procedure has significant morbidity, a prolonged recovery, and the threat of scarring and hemorrhage. In contrast, a transnasal endoscopic DCR has must less morbidity, no incision, and a quick recovery time. An endoscope DCR may be performed using lacrimal or sinus surgery instruments, a laser, or a balloon catheter. The endoscopic DCR ostium is smaller (5 to 9 mm.) than that of an open DCR. Because the DCR ostium is only 5 to 9 mm. (0.1969 to 0.354 inch) in diameter, a stent is required to keep the DCR ostium open after surgery. Otherwise postoperative inflammation and scarring may cause it to close.

In selecting a stent for this purpose, it is necessary to keep in mind the dimensions and properties of the canaliculi which are the narrowest part of the lacrimal system, as well as the properties of the silicone stent material and the technique for inserting the stent. An adult patient has canaliculi which are about 0.5 mm. (0.01969 inch) in diameter. It is possible however, to employ silicone tube stents which are somewhat larger in outer diameter, because there is a certain amount of resiliency, and give, in the tissue, and because tubular silicone stents tend to become thinner when placed under tension as they are pulled through the lacrimal system. The size of the silicone stent which can be used reaches an upper limit for the largest diameter stent which can be pulled through the canaliculi readily and without damaging the canaliculi. I have found that the largest diameter stent which can be so used is 0.053 inch.

It has been proposed in the prior art to use a silicone tube stent with a uniform diameter of 0.020 inch. However, this is too small a diameter to keep the endoscopic DCR ostium open.

A larger diameter tube with a diameter of 0.037 inch has also been used in the prior art. This larger diameter tube is still too small and soft to stent the balloon DCR ostium. Furthermore, the larger diameter causes irritation and epithelial defects on the cornea and conjunctiva where the tube lays against the eye in the medial canthus. It may also obstruct the drainage through the tiny canaliculi. The silicone tube comes with an attached rigid metal probe on each end. To place the tube in the lacrimal system, the probe is pushed through the punctum, canaliculus, lacrimal sac, DCR ostium into the nose. The probe is grasped in the nose and pulled down the nose and out the external naris. The probe pulls the attached silicone tube through the punctum, canaliculus, lacrimal sac and DCR ostium into the nose. The opposite end of the tube with its attached probe is brought through the opposing punctum and canaliculus, the lacrimal sac, and the DCR ostium into the nose. The probe attached to the opposite end is grasped in the nose and brought down the nose and out the external naris. The probe pulls the attached silicone tube through the punctum, canaliculus, lacrimal sac, and DCR ostium into the nose. The two ends of the tube are then cut 1½ cm. inside the external naris. The tube is left in place for about six months.

In an effort to stent the endoscopic DCR ostium with a larger diameter stent, which is too large to pass through the canaliculi, a short, more rigid stent, which can be placed from the nasal cavity, has been proposed. The short, large diameter stent is pushed from inside the nose through the endoscopic DCR ostium into the lacrimal sac. When in place, the stent extends from the lacrimal sac through the endoscopic DCR ostium into the nose. A number of such stents have been tried. They have had several problems. They are difficult or impossible to push into place. They frequently fall out shortly after surgery. Attempts to fixate them on a silicone tube are only minimally helpful. These stents can induce inflammation, infection and scarring.

I previously designed a "fat" silicone tube that has a large diameter in the portion that stents a balloon DCR ostium. An example is shown in my copending application Ser. No. 08/547,792, filed Oct. 25, 1995. It has a small diameter in the segment that lies against the eye. The large diameter portion (usually 0.052 inch in diameter) cannot be pulled through the small diameter puncta and canaliculi without slipping off the probe. Therefore, each end of the tube has a long small diameter portion. The small diameter ends of the tube are attached to the probe. After the probe is grasped in the nose, it is pulled down the nose and pulls the attached small diameter end of the tube through the puncta, canaliculi, lacrimal sac, balloon DCR ostium into the nose. The small diameter end of the tube is then grasped in the nose. As the small diameter segment is pulled down the nose, it pulls the attached larger diameter portion of the tube through the narrow puncta and canaliculi, the larger lacrimal sac and DCR ostium into the nose. This is done with each end of the tube. When in place, the ends of the tube are cut 1½ cm. inside the external naris. The larger diameter segment of the tube will lie in the distal canaliculi, lacrimal sac, and balloon DCR ostium extending into the nose. The small diameter end of the tube will have been cut off.

However, there are two problems with this "fat" tube. In some patients it can be difficult to pull the large diameter segments through the canaliculi. If the canaliculi are somewhat narrow, the tubes may break when the surgeon exerts traction on the narrow distal segment in the nose in an attempt to pull the fat segment through the canaliculi into the lacrimal sac. A second problem is that pulling the large diameter segments through the canaliculi may stretch the canaliculi enough to damage them and cause fibrosis (scarring). In this case, the canaliculi will become stenotic (narrow) and obstruct tear drainage after the tube is removed. This results in tearing. In addition, a tube with a diameter larger than 0.053 inch is needed to stent the balloon DCR ostium in some cases. However, as has been explained, it is impossible to pull a tube with a diameter much larger than 0.053 inch through the canaliculi into the lacrimal sac.

If a silicone tube could be brought into the canaliculi from the nasal cavity, a much larger diameter tube could be used. However, during surgery, it is usually not possible to see the common canaliculus from inside the nose, even when viewed through an endoscope. It is certainly not possible to thread a silicone tube from the nose through the tiny common canaliculus. For this reason, silicone intubation from the nose through the lacrimal sac into the canaliculi has never been performed.

An early proposal to insert a large canula into the lacrimal system is shown in U.S. Pat. No. 2,154,968. This patent suggests the use of a spiral canula of thin metal wire, the external diameter of which may vary up to 5/32 of an inch. The spiral is tapered at one end to facilitate insertion into the lacrimal duct. A tube is inserted through the punctum, canaliculus, lacrimal sac, and nasolacrimal duct into the nasal cavity, and a wire is threaded through the tube. The end of the wire is pulled out the nostril and the spiral canula is threaded on the wire with its tapered end turned upward. A supporting sleeve is placed on the wire and the canula is drawn up into the nasolacrimal duct from the nasal cavity.

However, the canula of the U.S. Pat. No. 2,154,968 is not a stent; it is a conduit. It is made of hard metal, not from silicone. The canula is not placed in an ostium surgically created to drain tears to the nasal cavity. In fact, the proposal is not clinically viable. It would lead to chronic infection and damage and the duct would close up after removal of the spiral canula. Moreover, the procedure suggested in the U.S. Pat. No. 2,154,968 would be very difficult for a surgeon to perform. For example, the surgeon would not be able to see that the canula is properly positioned, because visualization of the nasolacrmal duct is blocked by the inferior turbinate.

U.S. Pat. No. 5,437,625 discloses a device for intubation in the form of a single flexible silicone tube including a central thinner soft segment and a pair of larger diameter end segments with free ends which are sharp-pointed and sealed closed. The end segments have an outer diameter of 0.5–0.7 mm. (0.0197–0.0276 inch). The end segments have small cuts which receive metal probes extending to the closed tips during intubation. It has been found that the sharp-pointed end of the end segments, being rigid and hard, traumatize, and are too damaging to the canaliculi.

U.S. Pat. No. 4,305,395 teaches the use of metal probes inserted through openings in the side walls of polyamide tubular sheaths attached to the ends of a length of silicone rubber tubing. The tips of the probes abut the closed distal ends of the tubular sheaths. The tubing is then positioned in the lacrimal system by passing the probes inserted in the sheaths through the lacrimal system from above into the nose. The probes are removed, and the sheaths are grasped and pulled to position the tubing in the lacrimal system.

U.S. Pat. No. 4,380,239 is another example of the use of probes for the intubation of a silicone rubber tube. The probes, which are formed of steel wire, are inserted into the open end of the tube to facilitate insertion of the tube though a canaliculus into the lacrimal duct.

In the methods of the U.S. Pat. Nos. 4,305,395 and 4,380,239, the sheaths or probes must be pulled from the nostril, and during the procedure epistaxis and bone fracture of the inferior nasal concha sometimes occurs.

The silicone lacrimal stents of the prior art are tubular. Because a tube can only be manufactured by a molding process when the entire tube is of uniform diameter, a tube with a variable diameter can only be made by an extrusion process. The less reliable extrusion process allows tubes to be made when the variation in outside diameter is minimal. However, extrusion alone is not a feasible process where, as in the present invention, there is a large variation in the diameter of stent segments. Moreover, tubular extruded stents have a surface which is rougher than the surface possible from a molded stent. The extrusion process is also costly, because a significant percentage of extruded tubes do not conform to the specified diameter and must be discarded.

SUMMARY OF THE INVENTION

It is the object of the invention to provide a method for inserting a new kind of lacrimal stent having a very large diameter segment which has an outer diameter greater than the largest diameter stent which can be pulled through the canaliculi readily and without damaging the canaliculi.

It is a further object of the invention to provide a method for inserting the very large diameter stent segment into the patient's ostium from the nasal cavity (transnasal insertion).

A first embodiment of the lacrimal stent of the invention is an elongated soft silicone member having a very large diameter end segment with an outer diameter which is larger than the largest diameter stent which can be pulled through the patient's canaliculi readily and without damaging the canaliculi—that is, larger than 0.053 inch and smaller than the inner diameter of a DCR ostium created between the lacrimal sac and the nasal cavity. The elongated member includes additional segments which have outer diameters which are smaller than 0.053 inch. The additional segments include a relatively thin central segment, which will lie on the eye between puncta and in the canaliculi when the stent is installed. One end of the central segment is connected to an end of the very large diameter end segment through a short transition segment. The other end of the central segment is connected through a second short transition segment to an end of a moderate diameter segment, the other end of which is connected to a distal segment. A lumen extends from the distal end of the member partway down the length of the distal segment. The remainder of the member, including the rest of the distal segment, the moderate diameter segment, the transition segments, the central segment, and the very large diameter end segment are all solid. For this reason, the elongated soft silicone member is referred hereinafter as a "rod". In a preferred embodiment of the silicone rod, the very large diameter end segment has an outer diameter of 0.075 inch.

In a second embodiment of the lacrimal stent, the flexibility of the very large diameter segment is enhanced by a lumen extending from the free end of the very large diameter segment to a point just short of the first named transition segment or even for the entire length of the segment. In view of the substantially solid structure of the stents of these embodiments, except for the lumens in their distal segments, and, in the case of the second embodiment, the lumen in its very large diameter segment, it is possible to economically manufacture the entire stent by a molding process. Alternatively, the stents can be made in a process in which only the portion of the stent with the greatest variation in diameter—the thin central segment and the transition segments at each of its ends—is molded. The very large diameter, moderate diameter and distal segments are extruded and the separate pieces are fused together by injecting liquid silicone at all the junctions.

A first embodiment of the method of intubation or inserting the silicone rod stent of the invention comprises pulling the silicone rod stent from the distal end up through the patient's nose, ostium, lacrimal sac, common canaliculus, one of the patient's canaliculi and one of the patient's puncta. The distal end of the silicone rod stent is then pushed through the other of the patient's puncta, the other of the patient's canaliculi, the patient's common canaliculus, the patient's lacrimal sac, ostium and nasal cavity. The surgeon then grasps the distal end of the stent in the nasal cavity and pulls the stent down the patient's nose and out the patient's external naris, thereby pulling the moderate diameter segment through the nasal cavity, ostium, lacrimal sac, common canaliculus, one of the canaliculi, one of the puncta, the other of the puncta, the other of the canaliculi, the common canaliculus, the lacrimal sac, ostium and the nasal cavity, and pulling the very large diameter end segment up through the nasal cavity and ostium and into lacrimal sac. As a result, the very large diameter segment and the moderate diameter segment are positioned in the lacrimal sac, ostium, and nasal cavity; and the thin central segment is positioned in the palpebral fissure between the patient's puncta and in the superior and inferior canaliculi and the common canaliculus. It will be observed that it was not necessary to move the very large diameter end segment through the puncta and canaliculi.

The step of pulling the silicone rod stent from the distal end up through the nose is accomplished by using a semi-rigid sheath enclosing a removable metal rod. The metal rod has a head with a diameter greater than the diameter of the sheath adjacent the proximate end of the sheath and a distal end extending out the distal end of the sheath. The sheath enclosing the metal rod is pushed, distal end first, through one of the patient's puncta, one of the canaliculi, the common canaliculus, the lacrimal sac and the ostium into the nasal cavity. The surgeon reaches up the patient's nose and grasps the distal end of the metal rod and pulls the sheath and metal rod down the patient's nose until the distal ends of the metal rod and sheath are just outside the patient's external naris. The metal rod is then removed by pulling the rod by its head at its proximate end. The distal end segment of the silicone rod is then threaded into the distal end of the sheath. The sheath is then pulled by the surgeon back up the nose and out said one of the patients canaliculi and said one of the patient's puncta until the distal segment of the silicone rod is available to the surgeon outside the eye. The sheath is then removed from the distal segment of the silicone rod stent, and the surgeon then pulls the distal segment further out the eye.

The step of pushing the silicone rod back through the other punctum, the other canaliculus, the common canaliculus, the lacrimal sac, the ostium, and the nasal cavity involves the use of a metal probe having a thin distal portion. The distal portion of the probe is used to puncture the sidewall of the distal segment of the silicone rod stent 10 mm. from the distal end of the stent and is then inserted in the lumen until 7 mm. of the probe is within the lumen, leaving a 3 mm. end portion of the distal segment of the silicone rod stent between the end of the probe and the end of the silicone rod. The distal segment of the silicone rod stent and probe are then pushed through the patient's lacrimal system from above. The surgeon then grasps the 3 mm. end portion of the distal segment, which does not enclose the probe, and pulls the silicone rod downwardly while removing the probe with an upward movement. In prior art methods, such as is shown in U.S. Pat. Nos. 5,437,625 and 4,305,395, where the probe extends to the closed ends of the distal segment, it is more difficult for the surgeon to pull downwardly on the distal segment of the stent while pulling upwardly on the probe.

The surgeon continues pulling the silicone rod stent until the moderate diameter segment is pulled through the DCR ostium, the lacrimal sac, the common canaliculus, one canaliculus, one punctum, the other punctum, the other canaliculus, the common canaliculus, the lacrimal sac, the DCR ostium and into the nasal cavity. Meanwhile, the very large diameter end segment of the rod stent is pulled from the nasal cavity through the DCR ostium and into the lacrimal sac. Both the very large diameter and moderate diameter segments are thus positioned to stent the DCR ostium, while the central segment lies on the eye between the puncta and in the canaliculi.

A second method of inserting the lacrimal stent begins in the same way as the first method. After the sheath is in place in the lacrimal system, the distal lumen of the distal segment of the silicone rod is slipped on the thin distal portion of the metal probe, and the distal segment is swaged on the thin distal portion. The surgeon threads the proximate end of the probe into the distal end of the sheath until the proximate end of the probe emerges from the proximate end of the sheath. The surgeon grasps the proximate end of the probe and pulls the probe further out the sheath, thus pulling the swaged on distal segment into the sheath. After the distal segment of the stent has been pulled well up into the sheath, the surgeon grasps the sheath with one hand and the stent with the other hand. He then pulls the sheath back up the nasal cavity and out the superior canaliculus and superior punctum. This maneuver brings the probe and the distal segment of the stent through the DCR ostium, the lacrimal sac, the common canaliculus, the superior canaliculus, and the superior punctum. The surgeon then removes the sheath from the probe and the distal segment of the stent and grasps the distal segment of the stent. He pulls the distal segment of the stem further out the superior canaliculus and the superior punctum.

The surgeon next pushes the proximate end of the probe, with the stent still swaged on the distal end of the probe, into the inferior punctum, the inferior canaliculus, the common canaliculus, the lacrimal sac, and the DCR ostium into the nasal cavity.

The surgeon then reaches up the nasal cavity and grasps the probe and pulls the probe down the nasal cavity and out the external naris. The surgeon then removes the probe from the distal segment of the stent and pulls the distal segment further down the nasal cavity and out the external naris. This brings the moderate diameter segment of the stent through the superior canaliculus, the superior punctum, the inferior punctum, the inferior canaliculus, the common canaliculus, the lacrimal sac, and the DCR ostium into the nasal cavity. Meanwhile, the very large diameter end segment of the stent is pulled from the nasal cavity through the DCR ostium into the lacrimal sac. Both the very large diameter and moderate segments of the stent are thus positioned to stent the DCR ostium with the central segment of the stent lying on the eye between the puncta and in the canaliculi.

BRIEF DESCRIPTION OF THE DRAWINGS

FIGS. 19–22 illustrate additional steps of the method of FIGS. 16–18.

DETAILED DESCRIPTION

Figure 1:
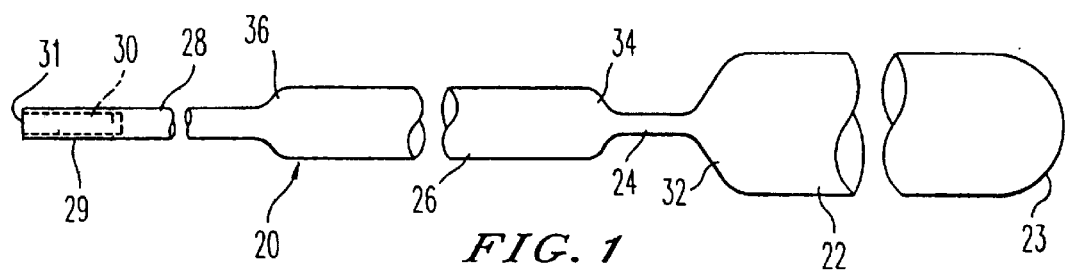
FIG. 1 is a view of a first embodiment of a lacrimal stent of the invention (not drawn to scale)

A first embodiment of a lacrimal stent of the invention is shown in FIG. 1. The stent 20 is formed of silicone rubber and has a very large diameter end segment 22 at one end. The phrase "very large diameter" is used to signify that segment 22 has an outer diameter which is larger than the largest diameter stent which can be readily pulled through the canaliculi without damaging the canaliculi. In the case of a typical adult patient, the canaliculi have an inner diameter of about 0.5 mm. (0.01969 inch); and the largest stent which can be pulled through the patient's canaliculi readily and without damage to the canaliculi is 0.053 inch (1.346 mm.). Accordingly, the diameter of very large diameter segment 22 is greater than 0.053 inch. In a preferred embodiment, the outer diameter of very large diameter segment 22 is 0.075 inch (1.905 mm.); and segment 22 is 12 cm. long (4.724 inches). The end 23 of segment 22 is smoothly rounded. In order to enhance the flexibility of segment 22, in a second embodiment of stent 20 shown in FIG. 1A, a lumen 37 of 0.025 inch diameter is formed, extending from end 23 to a point 37a 5 mm. from the opposite end of segment 22 or for the entire length of segment 22.

Figure 1A:
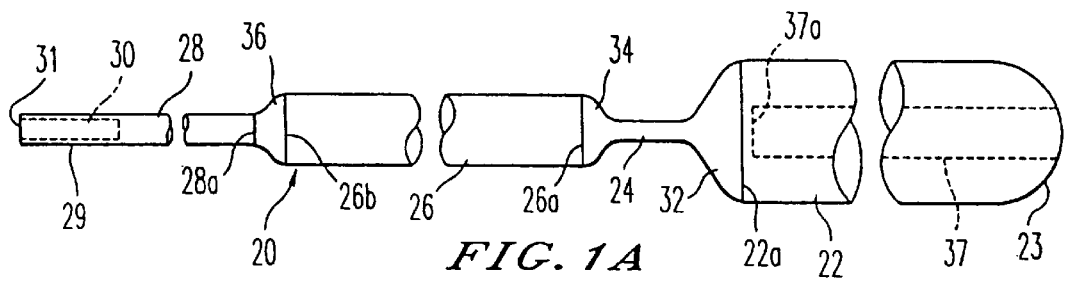
FIG. 1A is a view of a second embodiment of a lacrimal stent of the invention (not drawn to scale)

In both embodiments as shown in FIGS. 1 and 1A, the other end of segment 22 is connected to an end of a relatively thin central segment 24, which has an outer diameter of 0.030 inch (0.762 mm.) and a length of 20 mm. (0.787 inch). When stent 20 is installed, thin central segment 24 will lay against the eye in the medial canthus and in the canaliculi. The 0.030 inch diameter of segment 24 avoids irritation and epithelial defects which have been associated with larger diameter segments in this location and does not obstruct tear flow through the narrow canaliculi.

The other end of central segment 24 is connected to an end of a moderate diameter segment 26, the outer diameter of which can be pulled through the patient's canaliculi readily and without damaging the canaliculi. In the preferred embodiment, the outer diameter of moderate diameter segment 26 is 0.045 inch (1.143 mm.); and the length of segment 26 is 15 cm. (5.906 inches).

The other end of moderate diameter segment 26 is connected to an end of distal segment 28. This segment has the same outer diameter of 0.030 inch (0.762 mm.) as central segment 24 and is 7 cm. (2.756 inches.) in length. Although the rest of distal segment 28 is formed of solid silicone, a lumen 30 is provided in the distal 3 cm. (1.181 inches) of distal segment 28. Lumen 30 is thus 3 cm. long, extending from the distal end 31 of distal segment 28, is bounded by a sidewall 29, and has an internal diameter of 0.013 inch (0.3302 mm.). However, lumen 30 may also extend the full length of distal segment 28.

Smoothly tapered transition zones 32, 34 and 36, which are 3 mm. in length, respectively connect very large diameter segment 22 to central segment 24, central segment 24 to moderate diameter segment 26, and moderate diameter segment 26 to distal segment 28.

Although lacrimal stents of the prior art are tubular, the first embodiment of stent 20 as seen in FIG. 1 is solid silicone except for the portion of distal segment 28 which contains lumen 30. In the second embodiment, stent 20 is solid silicone except for the portions of distal segment 28 and very large diameter segment 22 which contain lumens 30 and 37, respectively.

In view of the large variation in the outer diameters of the segments of stent 20, it is not possible to form the entire stent 20 by extrusion. Instead, stent 20 of FIG. 1 may be molded in its entirety. This results in more reliable and economical manufacture of the stent and better conformation with design specifications. A molded stent also has a smoother surface than the surface of a tubular extruded stent.

However, the stent may also be made by an alternative method which molds only the portion of the stent which has the largest variation in diameter, while extruding other portions. In particular, as seen in FIG. 1A, central segment 24 and adjacent transition segments 32 and 34 are molded as one piece, while very large diameter segment 22, moderate diameter segment 26, and distal segment 28 are extruded as three additional pieces. The pieces are aligned in the proper order. The ends of very large diameter segment 22 and transition segment 32 abut at line 22a and are enclosed within a mold which snugly engages segments 22 and 32. Liquid silicone is injected into the mold and solidifies to fuse the abutting ends together. Likewise, the ends of transition segment 34 and moderate diameter segment 26 abut at line 26a and are enclosed within a second mold which is snugly engaged with segments 34 and 26. Liquid silicone is injected into the second mold and solidifies to fuse the abutting ends together. The other end 26b of moderate diameter segment 26 is aligned with, but spaced from, end 28a of distal segment 28. A third mold snugly engages segments 26 and 28 adjacent ends 26b and 28a and encloses ends 26b and 28a and the gap there between. Liquid silicone is injected into the mold, filling the gap, and solidifies to form transition segment 36 and fuse segments 26 and 28 together. It is also possible to omit the gap, abut ends 28a and 26b, and form transition segment 36 within the third mold around the end of segment 28 as ends 28a and 26b fuse together. While these techniques results in transition segments 36 which only approximate the smoothly tapered configuration of transition segments 32 and 34, the shape of transition segment 36 is not critical and an inexact surface on segment 36 will not interfere with the operation of stent 20.

In the alternative method, distal segment 28 and very large diameter segment 22 are extruded as tubes. In order to form lumen 30 in distal segment 28, a pin is inserted at the location of lumen 30, and the remainder of the tube is filled with liquid silicone and permitted to solidify. Lumen 37 in very large diameter segment 22 is formed in the same way. When the lumen is to extend the entire length of the segment, this step is omitted.

Moderate diameter segment 26, which is shown as solid in FIG. 1a, may also be extruded as a tube. The lumen formed therein may extend the entire length of the segment, which lumen is closed by transition 34 at end 26a and by transition 36 at end 26b.

Figure 2:
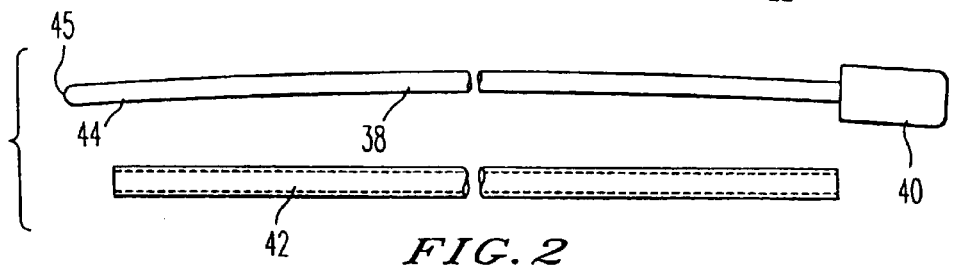
FIG. 2 is a view of a metal rod and sheath used in the methods of inserting the lacrimal stent of FIG. 1.
Figure 3:
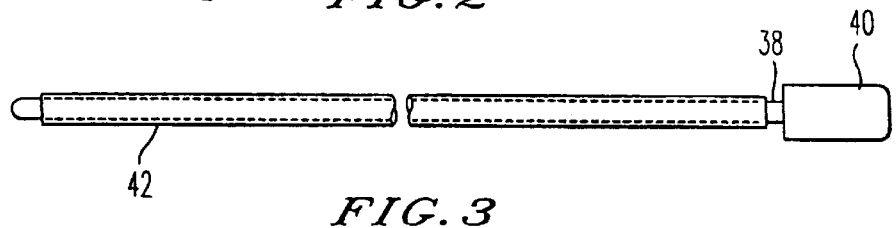
FIG. 3 is a view showing the rod of FIG. 2 inserted in the sheath of FIG. 2.

The processes of inserting stent 20 in a patient's lacrimal system require some special tools. As shown in FIG. 2, these include a metal rod 38, having a head 40, and a semi-rigid polyurethane sheath 42. Metal rod 38 is formed with a gentle arched curve and has an outer diameter of approximately 0.026 inch (0.6604 mm.). Rod 38 from the base of head 40 is 17.5 cm. (6.89 inches) long. Head 40 is 1 cm. long and has a diameter of 0.040 inch (1.016 mm.). Sheath 42 is 17 cm. (6.693 inches) long and has a very thin wall with an internal diameter of 0.035 inch (0.889 mm.). Rod 38 is inserted in sheath 42 as shown in FIG. 3. When head 40 abuts the end of sheath 42, the distal end section 44 of rod 38 extends out of the distal end of sheath 42 for 5 mm. (0.1969 inches) and has a smooth slightly rounded blunt tip 45.

Figure 4:
FIG. 4 is a metal probe used in the methods of inserting the lacrimal stent of the invention.

The methods of inserting the stent also use a metal probe 46 shown in FIG. 4. This probe has a diameter of 0.023 inch (0.584 mm.) and a distal portion 48 which has diameter of 0.015 inch (0.381 mm.) and a length of 10 mm. (0.3937 inch). The proximate end 49 of probe 46 is rounded, and the total length of probe 46 is 19 cm. (7.48 inches).

After the creation of a DCR ostium between the patient's lacrimal sac and nasal cavity endoscopically or by incision, the stent 20 is brought into place according to the methods of the invention.

Figure 5:
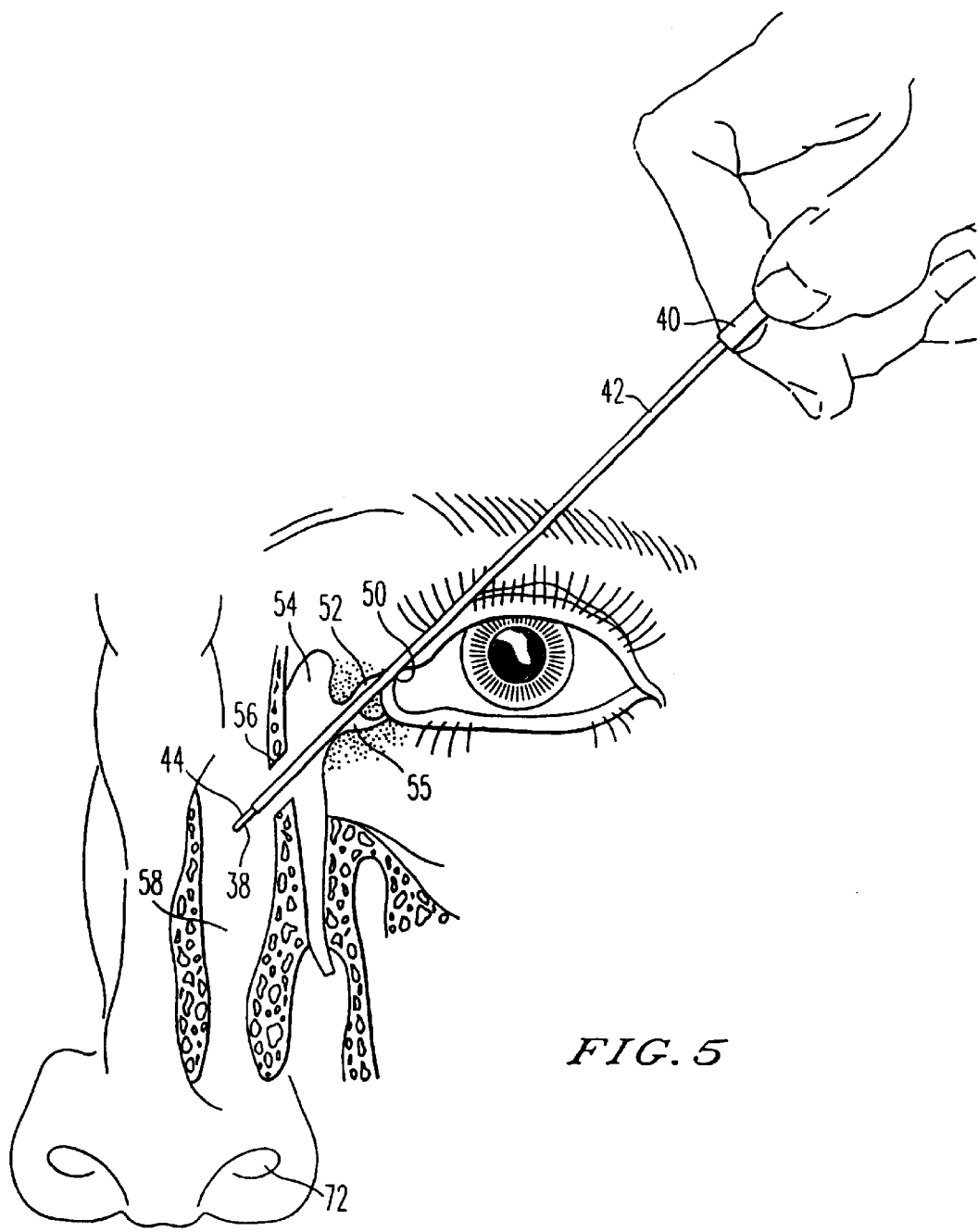
Figure 6:
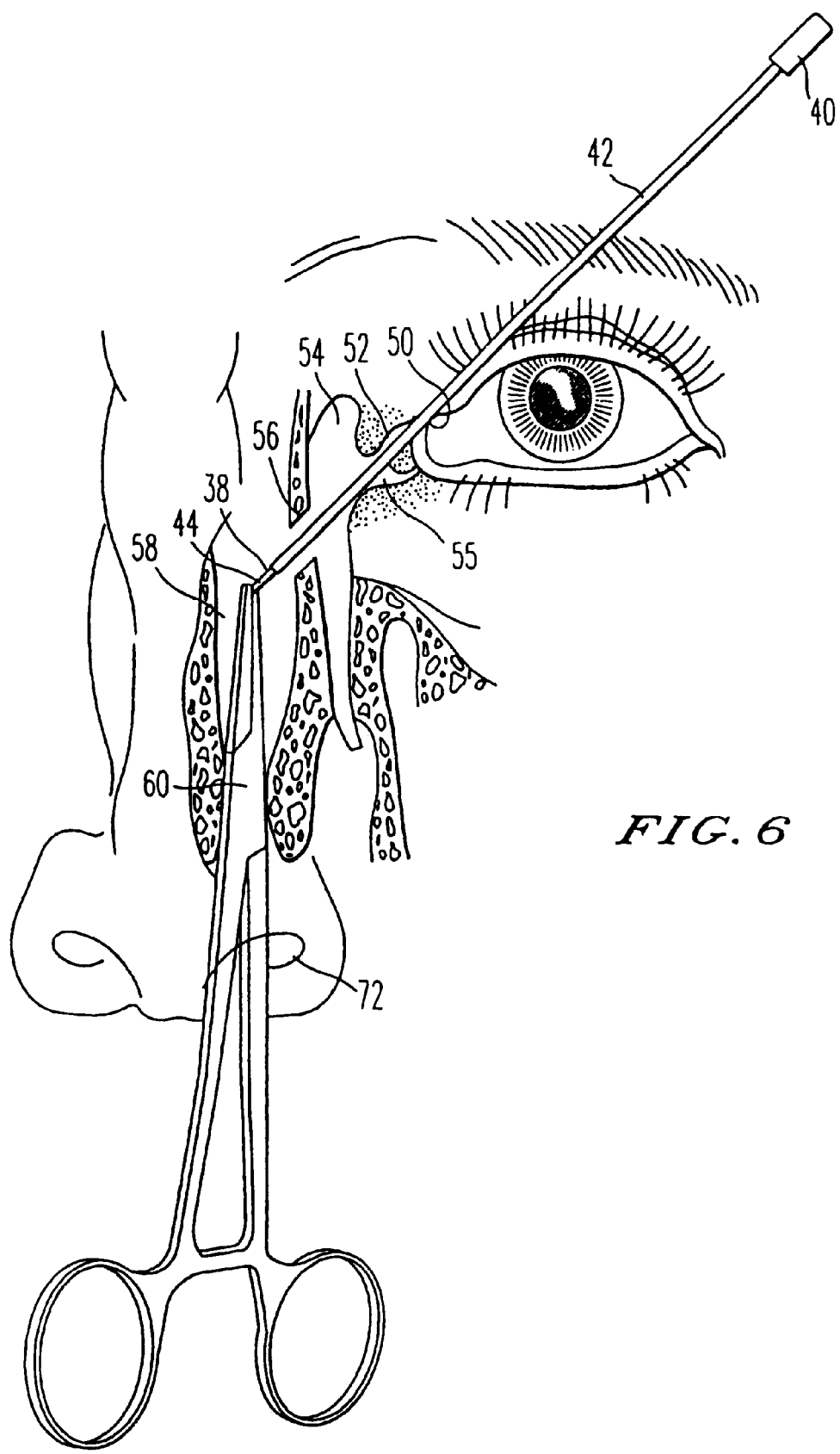

Referring to FIG. 5, according to a first embodiment of the method, the surgeon pushes rod 38 enclosed in sheath 42 through the patient's superior punctum 50, superior canaliculus 52, common canaliculus 55, lacrimal sac 54, and DCR ostium 56 into the patient's nasal cavity 58. As seen in FIG. 6, the surgeon reaches up the nose (nasal cavity 58) and grasps the end 44 of metal rod 38 with a hemostat 60, taking care to place hemostat 60 around distal end section 44 of metal rod 38 only so as not to damage sheath 42, and pulls rod 38 down the nose until distal end section 44 of rod 38 is just outside the patient's external naris 72. The surgeon then pulls metal rod 38 back out the proximal end of sheath 42 and removes it.

Figure 7:
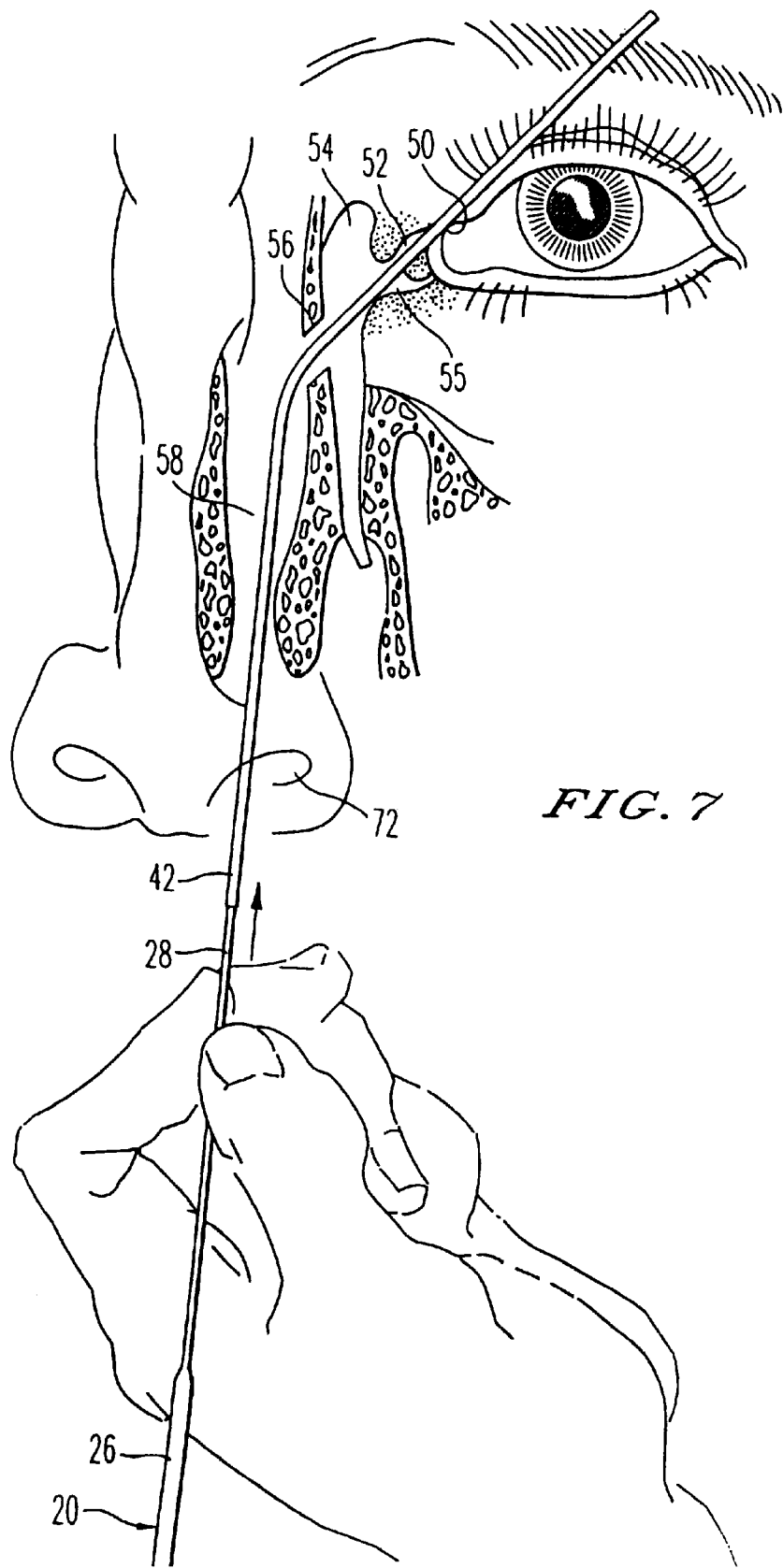
Figure 8:
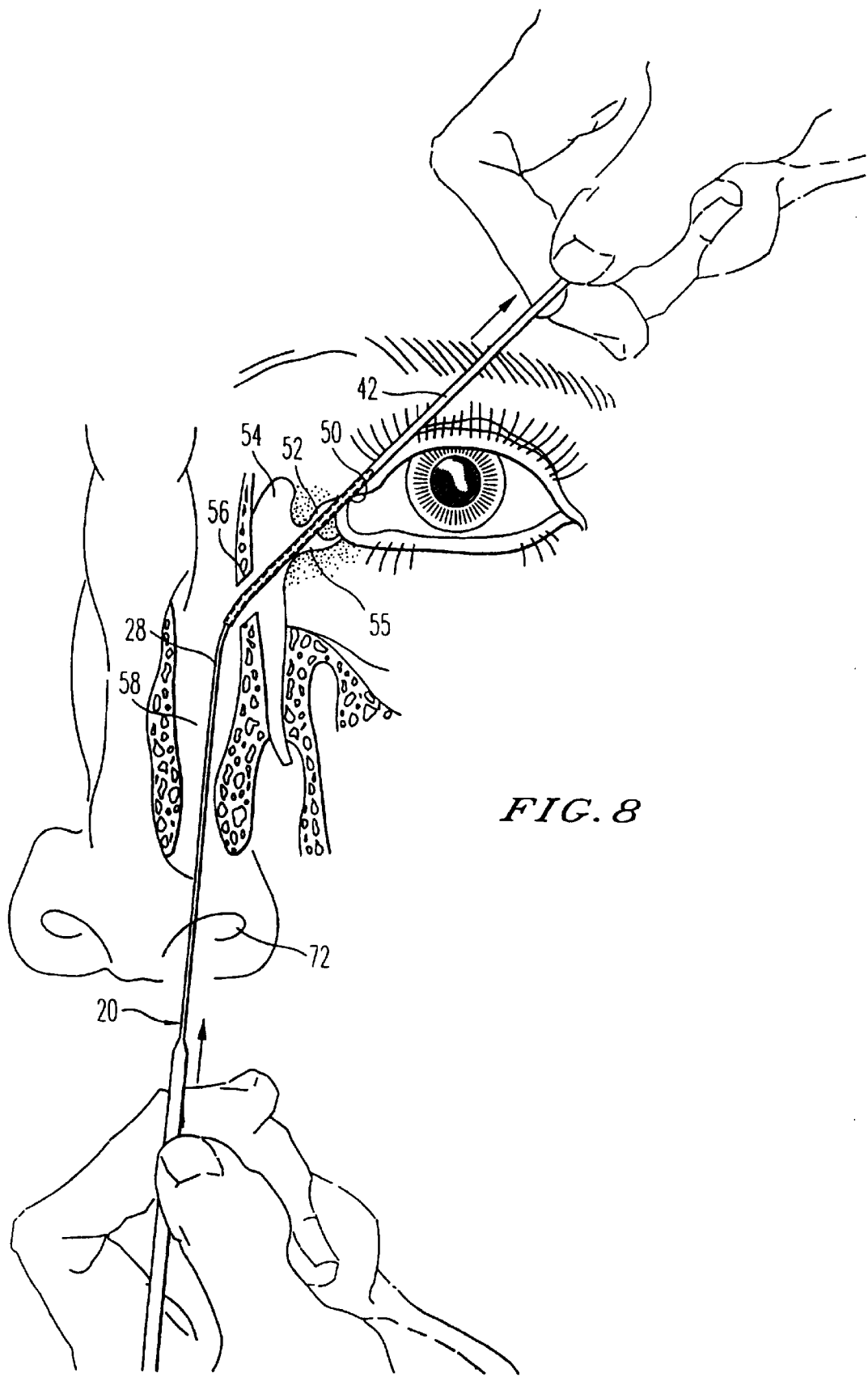
Figure 9:
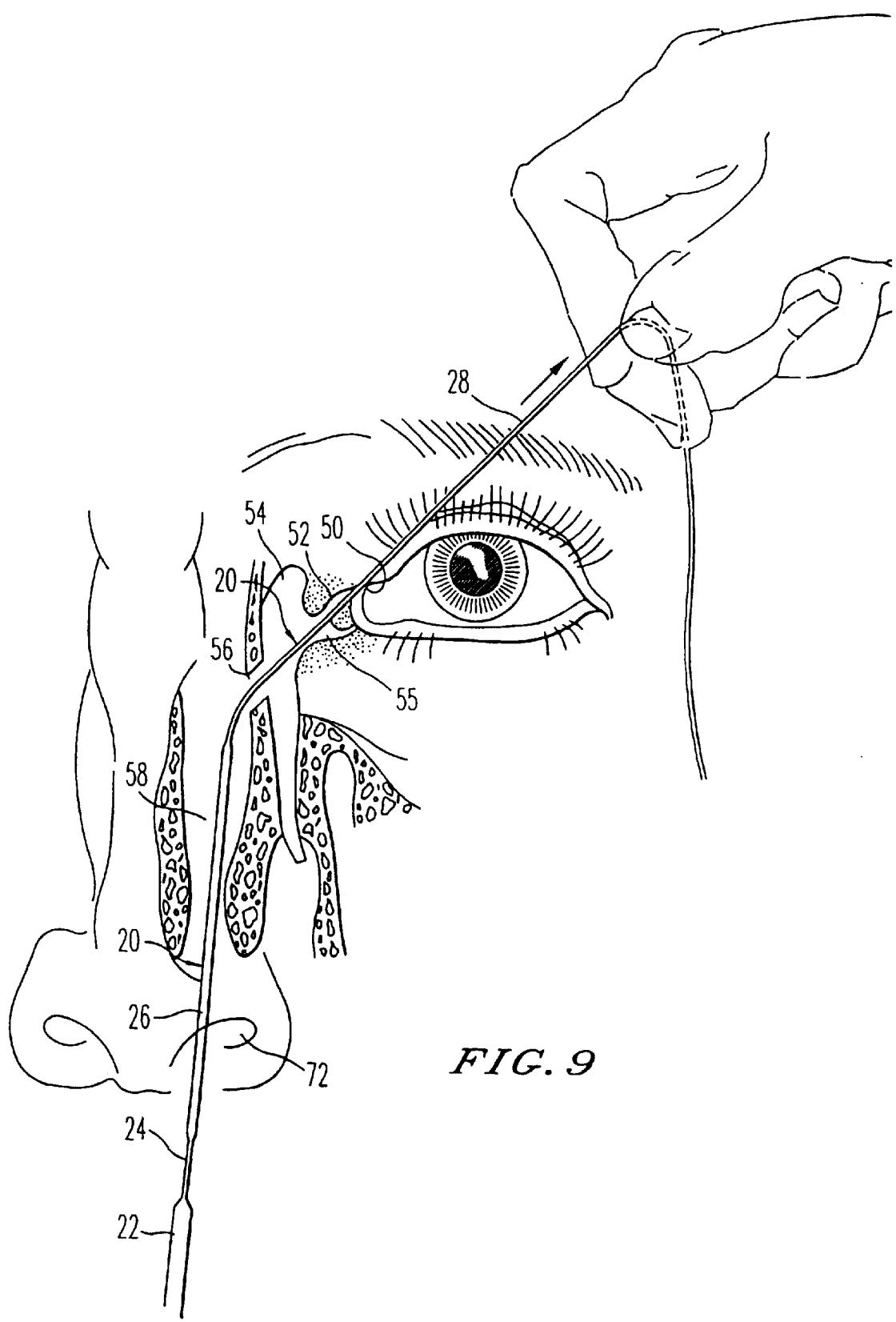

As seen in FIG. 7, the surgeon then threads distal end 28 of silicone stent 20 into the distal end of sheath 42 for several centimeters. FIG. 8 shows that the surgeon, grasping sheath 42 with one hand and stent 20 with the other hand, then pulls sheath 42 back up nasal cavity 58 and out superior canaliculus 52 and superior punctum 50. This maneuver brings distal segment 28 of stent 20 through DCR ostium 56, lacrimal sac 54, common canaliculus 55, superior canaliculus 52, and superior punctum 50. The surgeon then removes sheath 42 from distal segment 28 and, as seen in FIG. 9, grasps distal segment 28 and pulls stent 20 further out canaliculus 52 and punctum 50.

Figure 10:
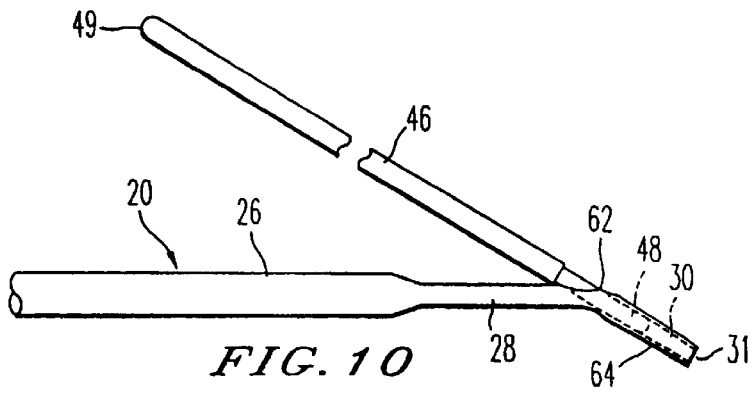
FIGS. 5–11 illustrate steps of a first embodiment of a method of inserting the lacrimal stent of the invention.

As illustrated in FIG. 10, the surgeon then bends distal segment 28 of stent 20 and, holding probe 46, punctures though sidewall 29 of lumen 30 of distal segment 28 with distal portion 48 of probe 46 to create an opening 62 at a point 10 mm. (0.3937 inch) from distal end 31 of distal segment 28. Distal portion 48 of probe 46 is then pushed through opening 62 until only 7 mm. (0.2756 inch) of probe portion 48 is positioned in lumen 30, leaving a distal 3 mm. (0.1181 inch) section 64 of the lumen unfilled by the probe.

Figures 11, 11A:
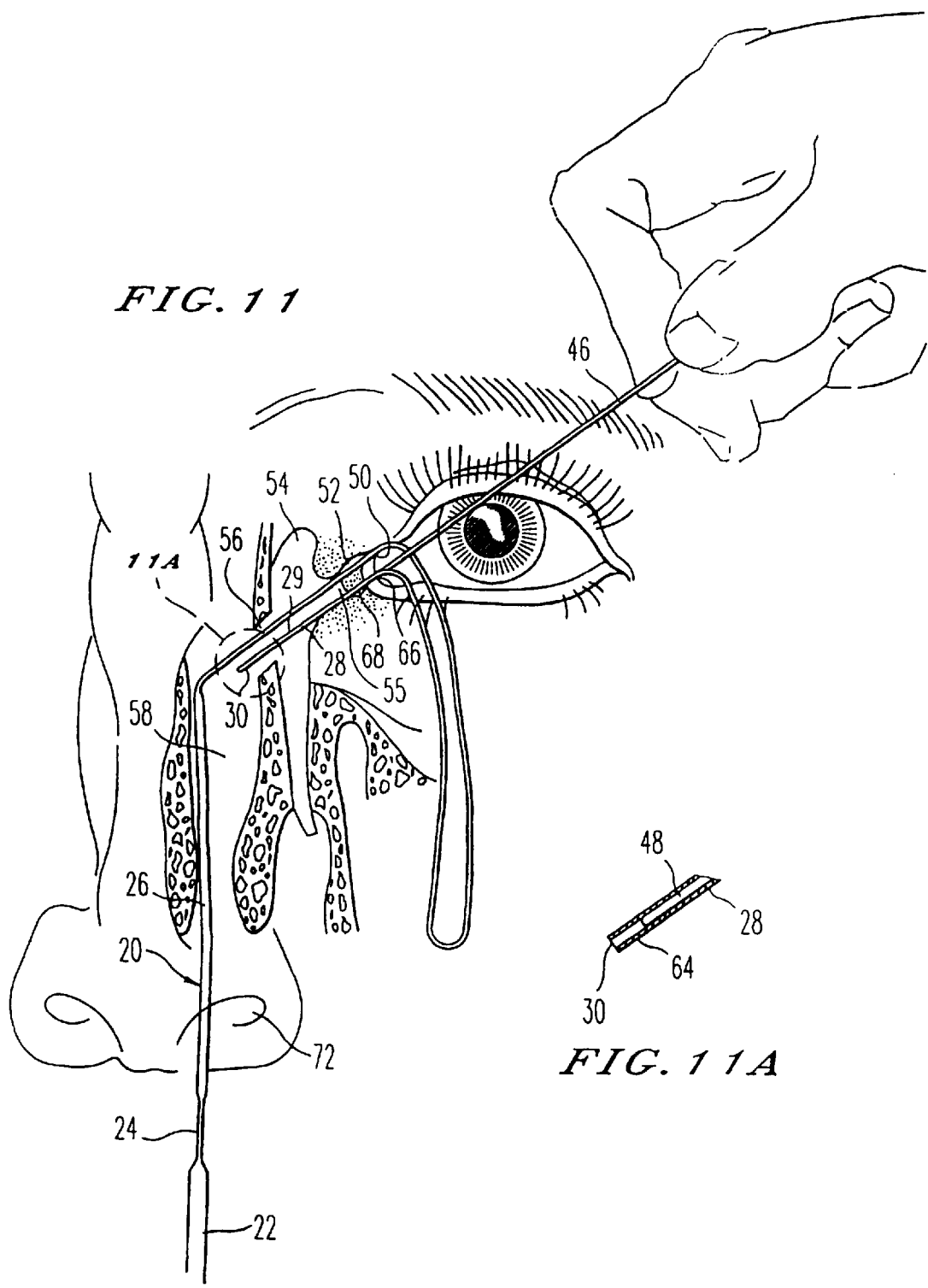
FIG. 11A is an enlargement of a detail of FIG. 11.

As seen in FIG. 11 and the enlarged detail of 11A, with the end of distal portion 48 of probe 46 inserted through sidewall 29 into lumen 30, the surgeon pushes probe 46 through inferior punctum 66, inferior canaliculus 68, common canaliculus 55, lacrimal sac 54 and DCR ostium 56 into nasal cavity 58.

Figure 12:
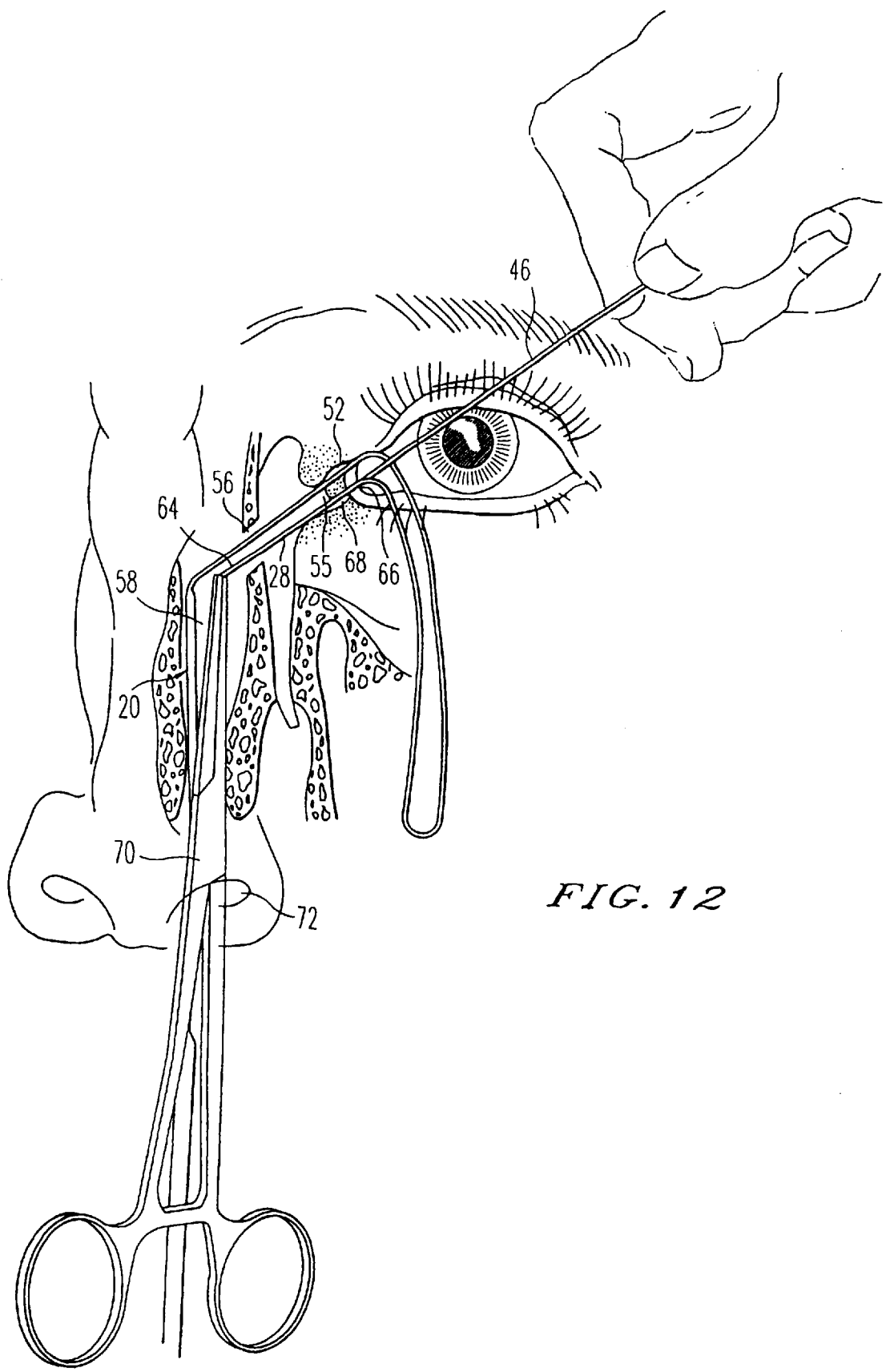
FIGS. 12–15 illustrate additional steps of the method of FIGS. 5–11.

The surgeon then reaches up nasal cavity 58 with a hemostat 70 (see FIG. 12) and grasps end section 64 of distal segment 28 and pulls stent 20 down nasal cavity 58 and out the external naris 72. As this is done, the surgeon pulls probe 46 upwardly out punctum 66 to remove it from lumen 30.

Figure 13:
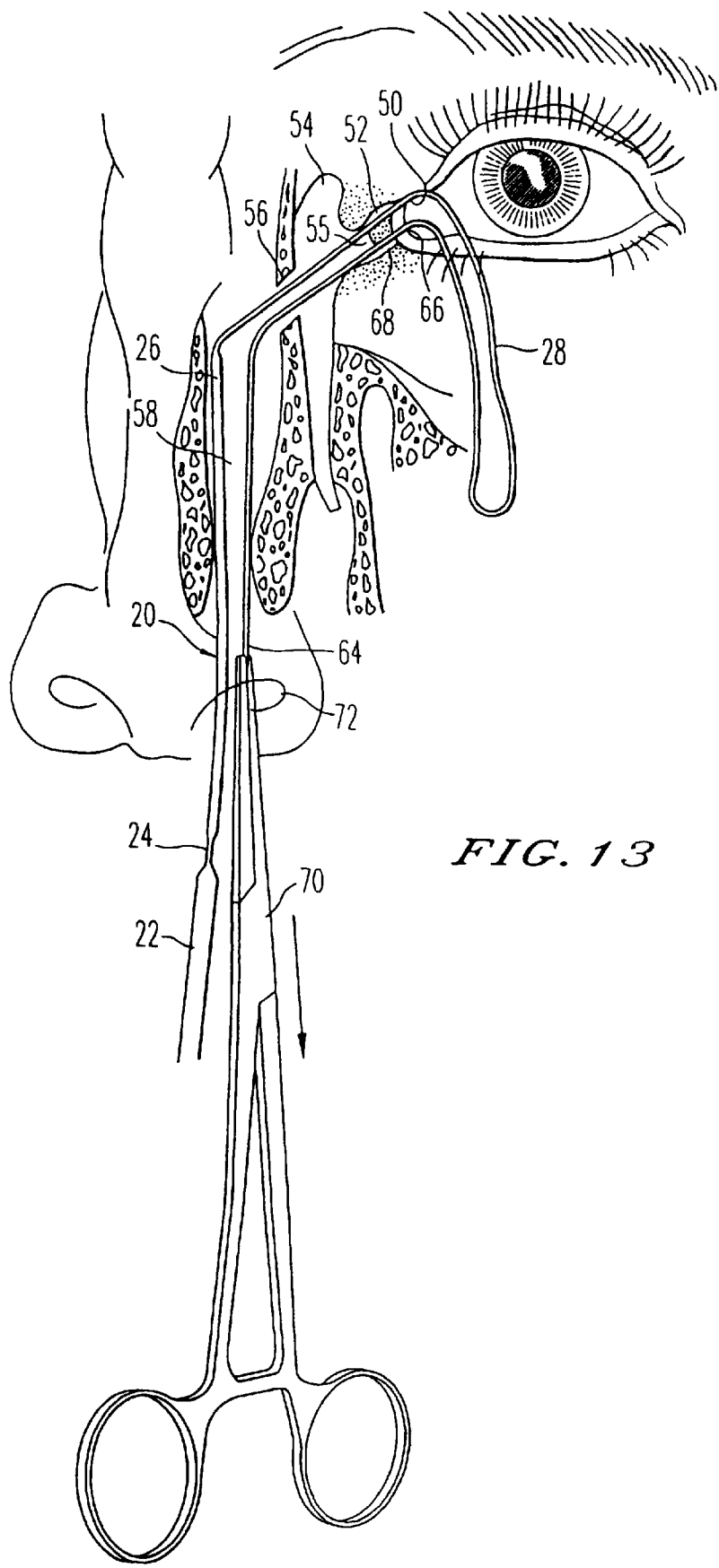
Figure 14:
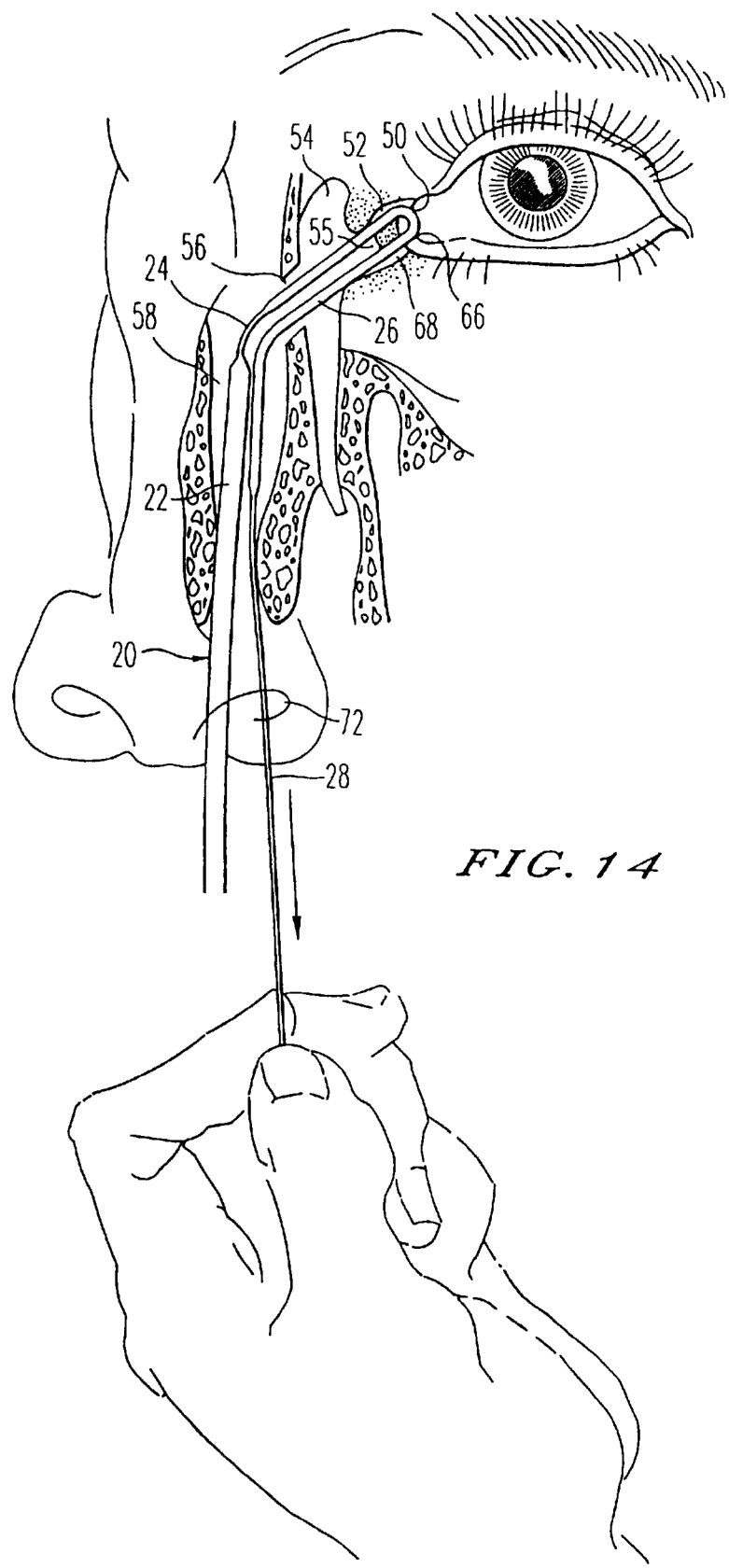

FIG. 13 shows that the surgeon then keeps pulling stent 20 out the nose. As the surgeon continues to pull, as seen in FIG. 14, he brings moderate diameter segment 26 through superior canaliculus 52, superior punctum 50, inferior punctum 66, inferior canaliculus 68, common canaliculus 55, lacrimal sac 54 and DCR ostium 56 into nasal cavity 58.

The surgeon continues pulling until very large diameter segment 22 is pulled into position in DCR ostium 56 with an end of segment 22 pulled through lacrimal sac 54 up against, but not into, the lacrimal sac end of common canaliculus 55 and the opposite end in nasal cavity 58. Moderate diameter segment 26 is positioned in DCR ostium 56 with an end in lacrimal sac 54 adjacent the lacrimal sac end of common canaliculus 55 and with the opposite end in nasal cavity 58. Central segment 24 is positioned to occupy the palpebral fissure between superior and inferior puncta 50 and 66 and in superior and inferior canaliculi 52 and 68 and common canaliculus 55.

A suture is used to tie the ends of segments 22 and 26 in nasal cavity 58 together. The two ends in the nasal cavity are then cut off about 1 cm inside external naris 72. This is the situation seen in FIG. 15.

This method solves several problems. It allows very large diameter segment 22 to stent DCR ostium 56, despite the fact that a segment with this large a diameter cannot be pulled through the canaliculi into lacrimal sac 54. This is because the distal segment end of stent 20 is brought through the canaliculi from the nasal side, making it unnecessary for very large diameter segment 22 with a diameter of 0.075 inch to traverse the small diameter canaliculi. The moderate diameter segment 26 with a diameter of 0.045 inch is the largest to pass through the canaliculi, which it can traverse readily, minimizing the possibility of damage to the canaliculi from stretching. Because moderate diameter segment 26 passes through the canaliculi relatively easily, it is unlikely that 0.030 inch central segment 24 or distal segment 28 will snap off as segment 26 is pulled through the canaliculi. It will be appreciated that the successful implementation of the method is made possible by the particular structural configuration and dimensions of stent 20.

A second and alternative embodiment of a method of inserting the lacrimal stent of the invention will now be described with reference to FIGS. 16–22.

The alternative method begins in the same way as the method of FIGS. 5–15. As shown in FIG. 5, the surgeon pushes rod 38 enclosed in sheath 42 through the patient's superior punctum 50, superior canaliculus 52, common canaliculus 55, lacrimal sac 54, and DCR ostium 56 into the patients nasal cavity 58. Metal rod 38 is then pulled down, as shown in FIG. 6, until distal end 44 of rod 38 is just outside the patient's external naris 72. The surgeon pulls metal rod 38 back out the proximal end of sheath 42 to remove it, leaving sheath 42 in place.

Figure 16:
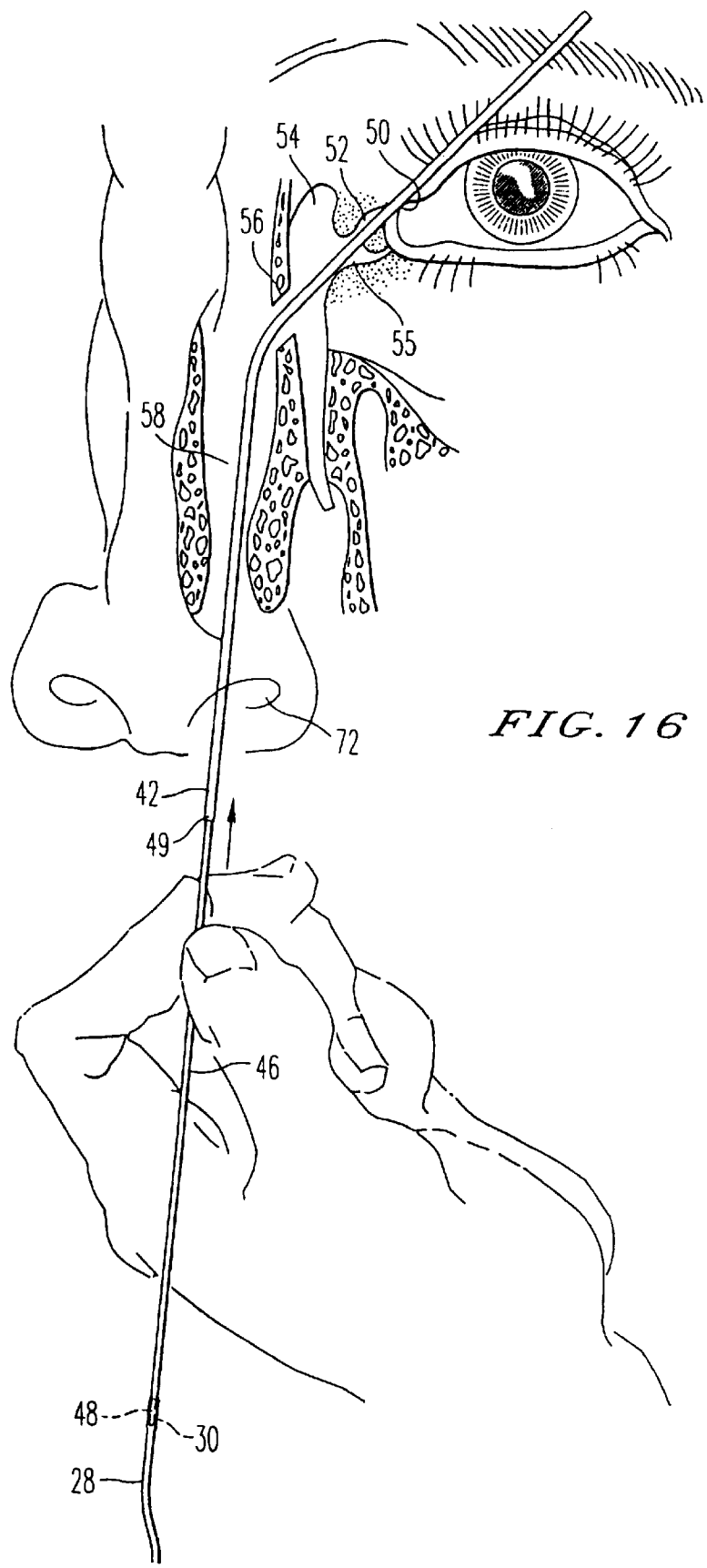
FIGS. 16–18 illustrate steps of a second embodiment of a method of inserting the lacrimal stent of the invention.
Figure 17:
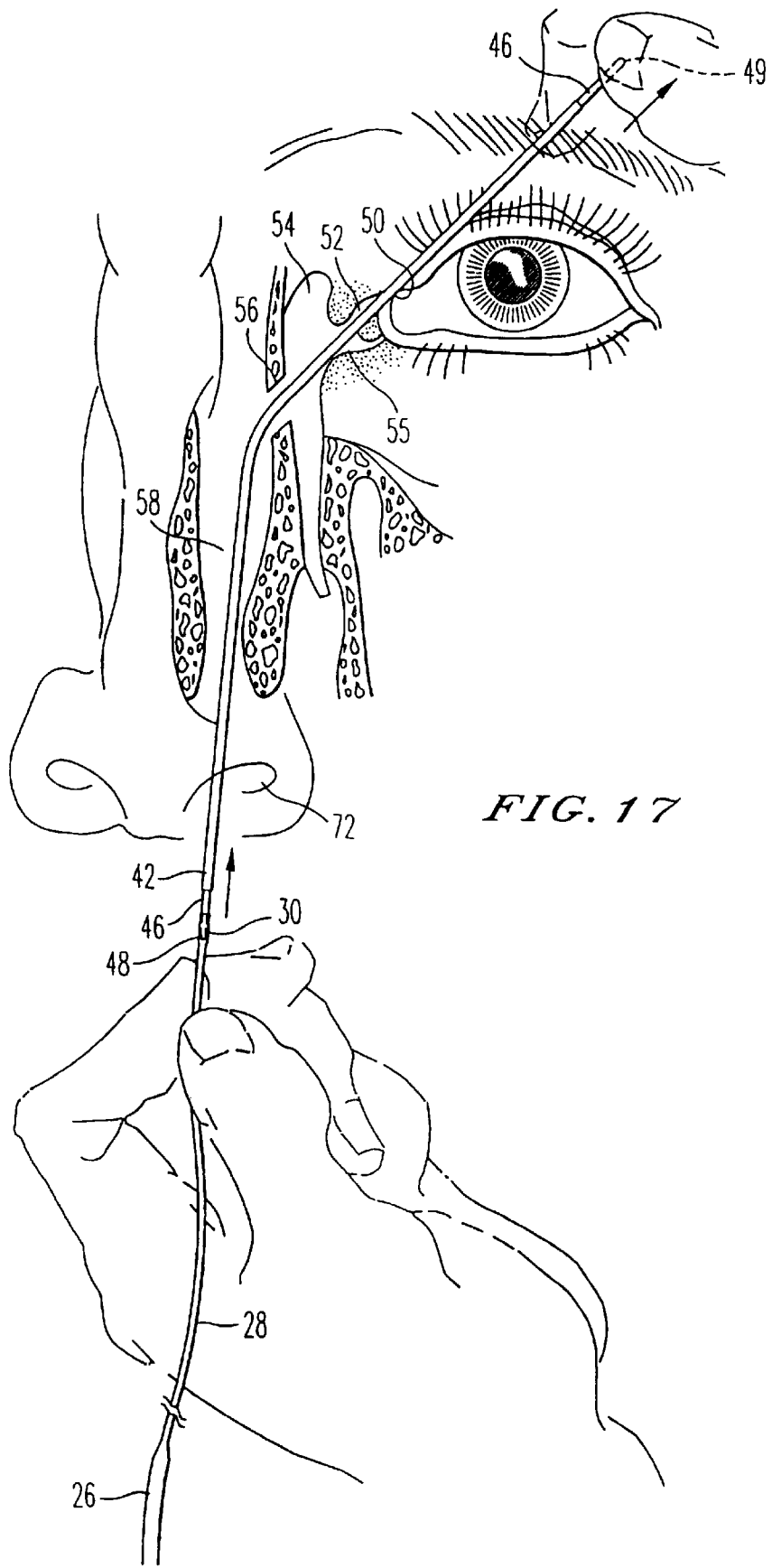
Figures 18, 18A:
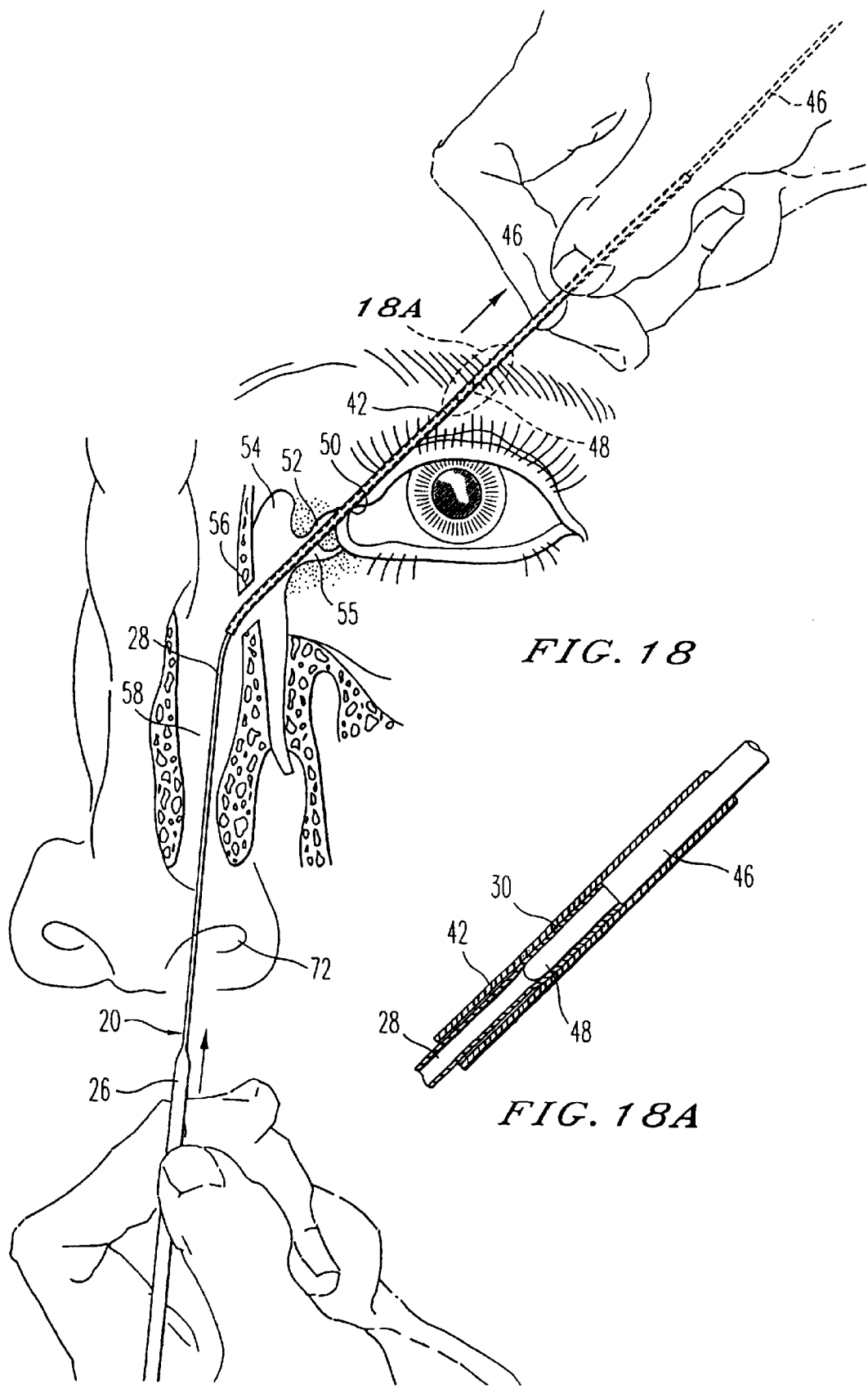
FIG. 18A is an enlargement of a detail of FIG. 18.

After the sheath is thus in place, according to the alternative method, the distal lumen 30 of distal segment 28 is swaged on the thin distal portion 48 of metal probe 46 as illustrated in FIG. 16. As seen in FIG. 16, the surgeon threads end 49 of probe 46 into the distal end of sheath 42 until the end 49 emerges from the proximal end of sheath 42 as seen in FIG. 17. The surgeon grasps end 49 of probe 46 and pulls probe 46 further out sheath 42, thus pulling swaged on distal segment 28 of stent 20 into sheath 42. After distal segment 28 has been pulled well up into sheath 42, the surgeon then, as shown in FIG. 18, grasps sheath 42 with one hand and stent 20 with the other hand and pulls sheath 42 back up nasal cavity 58 and out superior canaliculus 52 and superior punctum 50. This maneuver brings probe 46 and distal segment 28 through DCR ostium 56, lacrimal sac 54, common canaliculus 55, superior canaliculus 52 and superior punctum 50. FIG. 18A shows, in an enlarged view, distal segment 28 swaged on thin distal portion 48 of probe 46 within sheath 42.

The surgeon then removes sheath 42 from probe 46 and distal segment 28. As seen in FIG. 19, the surgeon grasps distal segment 28 and pulls stent 20 further out canaliculus 52 and punctum 50.

Figure 20:
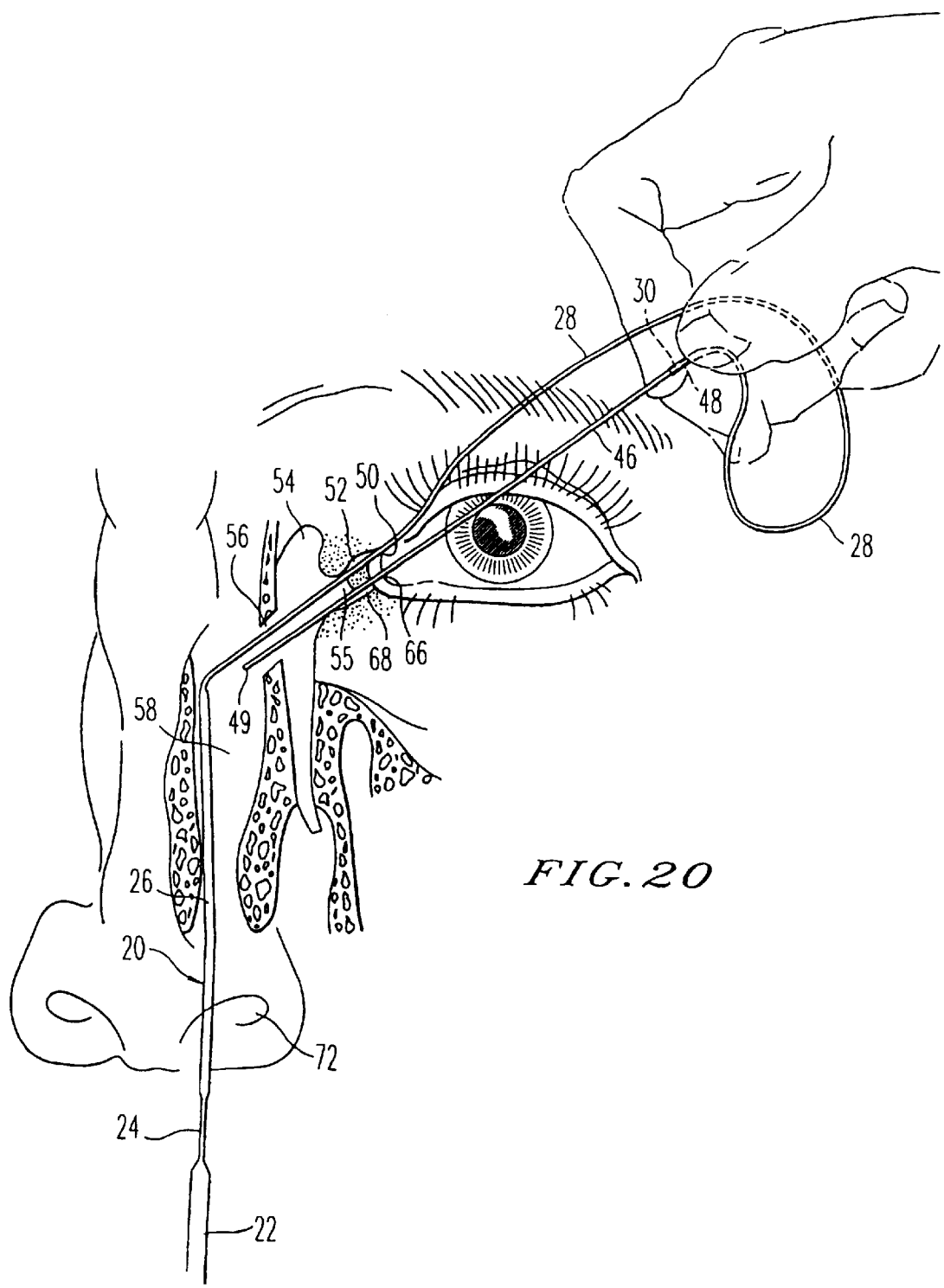
Figure 21:
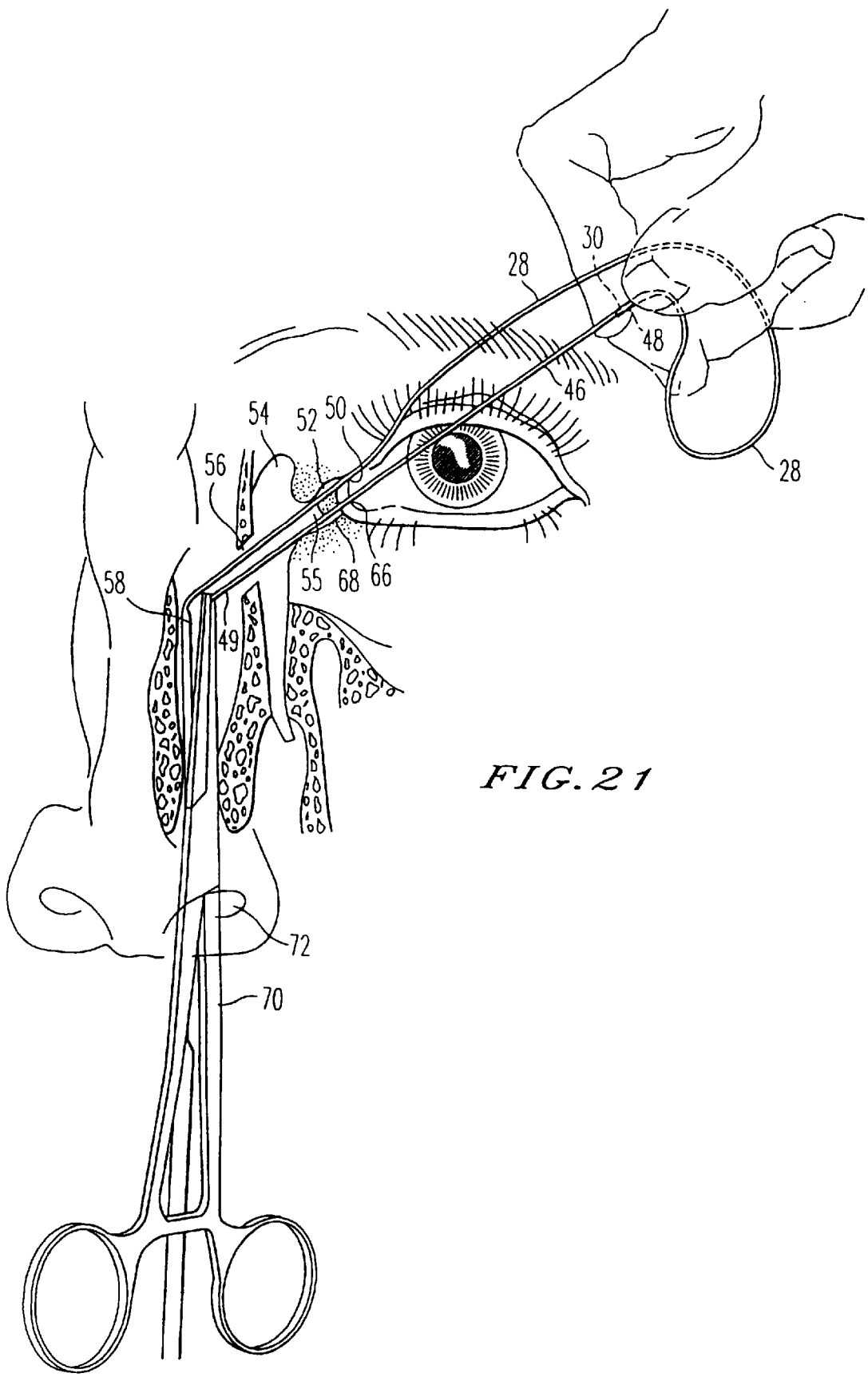
Figure 22:
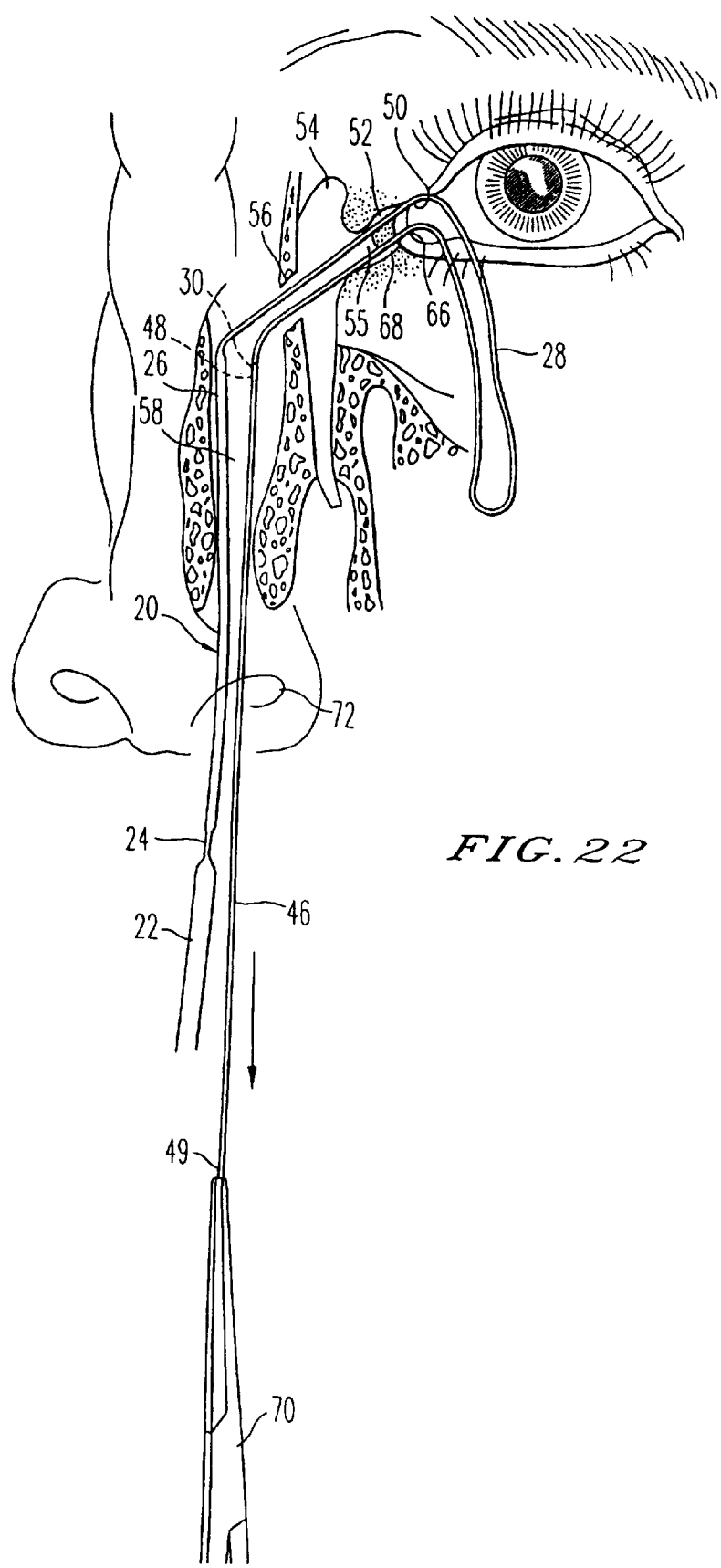

As illustrated in FIG. 20, the surgeon pushes end 49 of probe 46 into inferior punctum 66, inferior canaliculus 68, common canaliculus 55, lacrimal sac 54, and DCR ostium 56 into nasal cavity 58. The surgeon then reaches up nasal cavity 58 with hemostat 70 (see FIG. 21) and grasps probe 46. He then pulls probe 46 with swaged on distal segment 28 of stent 20 down nasal cavity 58 and out external naris 72 (see FIG. 22).

Figure 15:
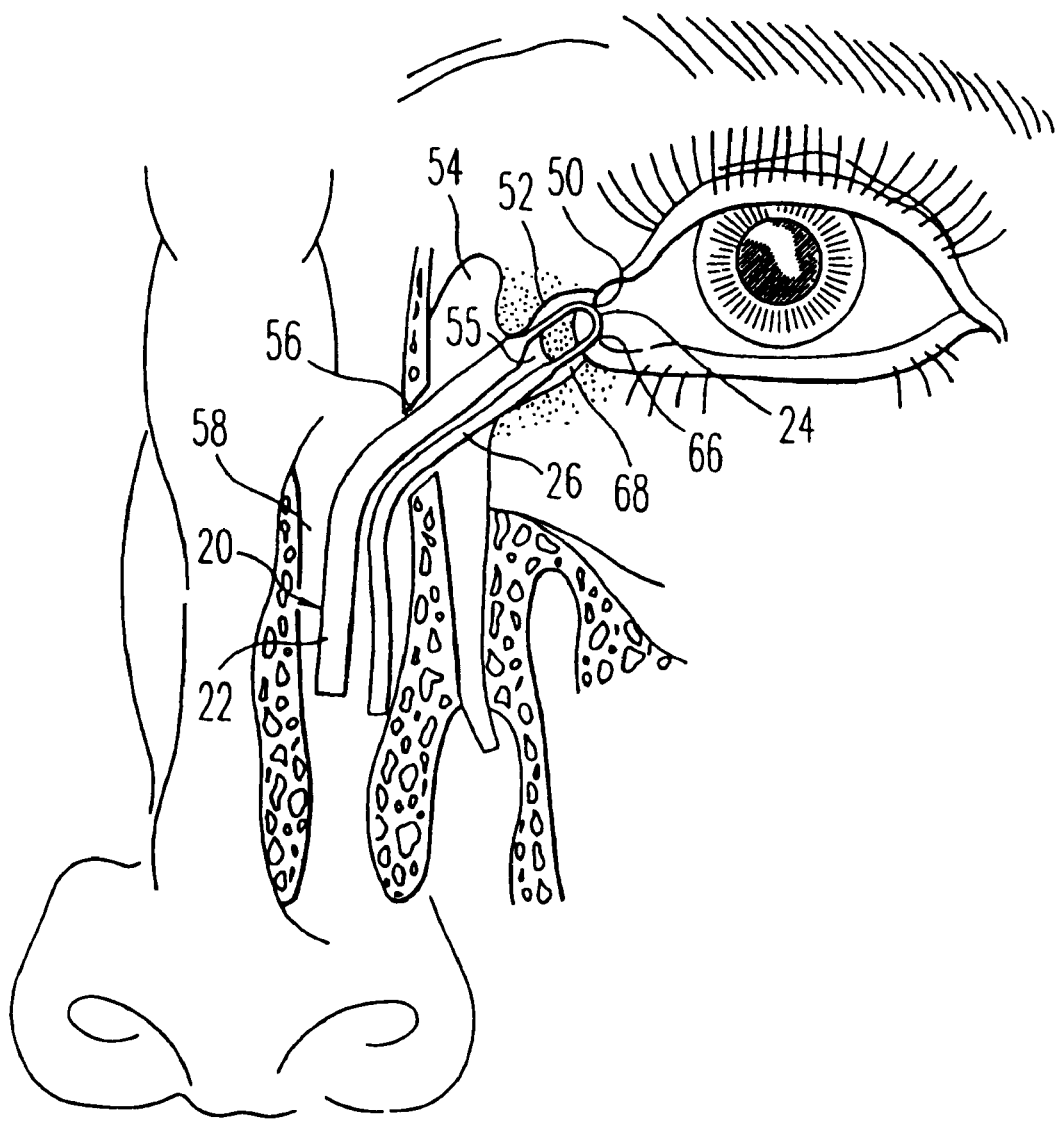

At this time, the surgeon removes probe 46 and pulls on distal segment 28 (now free of probe 46), moving it further down nasal cavity 58 and out external naris 72, thereby bringing moderate diameter segment 26 through superior canaliculus 52, superior punctum 50, inferior punctum 66, inferior canaliculus 68, common canaliculus 55, lacrimal sac 54, and DCR ostium 56 into nasal cavity 58. This is the same position attained in FIG. 14 of the first method of inserting the stent. The remaining steps of the method are the same as those described for the first method as illustrated in FIGS. 14 and 15.

In a further variation of the method, stent 20 could be manufactured with distal segment 28 already swaged on portion 48 of probe 46.

It should be understood that the foregoing description of the invention is intended merely to be illustrative and other modifications, embodiments and equivalents may be apparent to those skilled in the art without departing from the spirit and scope of the invention.

The invention claimed is:

1. A method of inserting lacrimal stent apparatus in a surgically formed ostium between a patient's lacrimal sac and nasal cavity, said stent apparatus comprising a silicone rod with proximate and distal ends and including a very large diameter end segment which at all times during said insertion of said stent apparatus has an outer diameter which is larger than the largest diameter stent which can be pulled through the patient's canaliculi readily without damaging the canaliculi, a moderate diameter segment having an outer diameter smaller than said largest diameter, a relatively thin central segment between said very large diameter end segment and said moderate diameter segment, and a distal segment between the distal end of said silicone rod and an end of said moderate diameter segment, said method comprising:

pulling said silicone rod from said distal end up through the patient's nose, the patient's ostium, the patients's lacrimal sac, the patient's common canaliculus, one of the patient's superior and inferior puncta, pushing said distal end of said silicone rod through the other of the patient's puncta, the other of the patient's canaliculi, the patient's common canaliculus, the patient's lacrimal sac, and the patient's ostium into the patient's nasal cavity, grasping said distal end of said silicone rod in the patient's nasal cavity and pulling said rod down the patient's nose and out the patient's external naris, thereby pulling said moderate diameter segment through said patient's nasal cavity, the patient's ostium, the patient's lacrimal sac, the patient's common canaliculus, said one of the said patient's canaliculi, said one of said patient's puncta, said other of said patient's puncta, said other of the patient's canaliculi, the patient's common canaliculus, the patient's lacrimal sac, the patient's ostium, and the patient's nasal cavity, and thereby pulling said very large diameter end segment up through the patient's nasal cavity, the patient's ostium, into the patient's lacrimal sac, whereby said very large diameter end segment and moderate diameter segment are positioned in the patient's ostium, nasal cavity and lacrimal sac and said thin central segment is positioned in the patient's palpebral fissure between the puncta, the superior and inferior puncta, the superior and inferior canaliculi and the common canaliculus.

2. The method of claim 1, wherein said one of said patient's canaliculi is the patient's superior canaliculus, said other patient's canaliculi is the patient's inferior canaliculus, said one of the patient's puncta is the patient's superior punctum and said other of the patient's puncta is the patient's inferior punctum.

3. The method of claim 1, wherein said step of pulling said silicone rod from said distal end up through the patient's nose comprises:

providing a semi-rigid sheath with open proximate and distal ends and a removable metal rod extending through said sheath with a distal end extending beyond said distal end of said sheath;

pushing said sheath containing said metal rod through one of the said patient's puncta, one of the patient's canaliculi, the patient's common canaliculus, the patient's lacrimal sac and the patient's ostium into the patient's nasal cavity;

reaching up the patient's nose, and grasping said distal end of said metal rod, and pulling the metal rod and said sheath down the patient's nose until said distal end of said metal rod is just outside the patient's external naris;

removing said metal rod by pulling it out said proximal end of said sheath;

threading said distal segment of said silicone rod into the distal end of said sheath;

pulling said sheath back up the nose and out of said one of the patient's canaliculi and puncta, bringing said distal segment of said silicone rob through said one of said canaliculi and said one of said puncta; and grasping said distal segment of said silicone rod and pulling the silicone rod further out said canaliculus and punctum.

4. The method of claim 3, wherein said distal segment has a lumen extending from said distal end for a portion of the length of said distal segment, said distal segment forming a sidewall of said lumen, and wherein said step of pushing said distal end of said silicone rod through the other of the patient's puncta comprises:

provilding a metal probe having a distal portion;

bending a portion of said distal segment of said silicone rod including said lumen at a first point spaced from said distal end of said silicone rod;

puncturing the sidewall of said distal segment at said first point and inserting said distal portion of said probe into said lumen in the direction of said distal end to a second point spaced from said distal end of said silicone rod;

pushing said distal portion of said probe within said distal segment of said silicone [tube] rod and said distal segment through said other of the patient's puncta, the other of the patient's canaliculus, the patient's common canaliculus, the patient's lacrimal sac and the patient's ostium into the patient's nasal cavity; and removing said probe as said distal end of said silicone rod is grasped in the patient's nasal cavity and pulled down.

5. The method of claim 4, wherein said distal segment of said silicone rod is 7 cm. long, has an outer diameter of 0.03 inch, wherein said lumen is 3 cm. long, wherein said lumen has an inner diameter of 0.013 inch, wherein said distal portion of said probe is 10 mm. long and has an outer diameter of 0.015 inch, and wherein said first point on said distal segment of said silicone rod is 10 mm. from said distal end of said silicone rod, 7 mm. of said probe being inserted within said lumen.

6. The method of claim 1, further comprising the step of tying the two ends of said silicone rod in the patient's nose and cutting off said ends within the patient's external naris.

7. A method of claim 1, wherein said very large diameter end segment has an outer diameter of 0.075 inch, a length of 12 cm., said central segment has an outer diameter of 0.03 inch and a length of 20 mm, said moderate diameter segment has inch and a length of 15 cm and said distal segment has an outer diameter of 0.03 inch length of 7 cm.

8. The method of claim 1, wherein said step of pulling said silicone rod from said distal end up through the patient's nose comprises:

providing a semi-rigid sheath with open proximate and distal ends and a removable metal rod extending through said sheath with a distal end extending beyond said distal end of said sheath;

pushing said sheath containing said metal rod through one of the said patient's puncta, one of the patient's canaliculi, the patient's common canaliculus, the patient's lacrimal sac and the patient's ostium into the patient's nasal cavity;

reaching up the patient's nose, and grasping said distal end of said metal rod [portion], and pulling the metal rod and said sheath down the patient's nose until said distal end of said metal rod is just outside the patient's external naris;

removing said metal rod by pulling it out said proximal end of said sheath;

swaging said distal segment on a distal portion of a metal probe, said distal portion being relatively thinner than the remainder of said probe, said probe having a proximate end;

threading the proximate end of said probe into the distal end of said sheath until the proximate end of said probe emerges from the proximate end of said sheath;

grasping said proximate end of said probe and pulling said probe further out the sheath, thus pulling said swaged on distal segment into said sheath;

grasping the sheath with one hand and said stent with the other hand and pulling said sheath back up the nasal cavity and out one of said patient's canaliculi and one of said patient's puncta;

bringing said probe and said distal segment through said DCR ostium, lacrimal sac, common canaliculus, said one of said patient's canaliculi and said one of said patient's puncta;

removing said sheath from said probe and distal segment of said distal segment;

grasping said distal segment, and pulling said distal segment further out the one canaliculus and said one punctum.

9. The method of claim 8, wherein said step of pushing said distal end of said silicone rod through the other of said patient's puncta, comprises;

pushing said proximate end of said probe, with said distal end of said silicone rod still swaged on said distal end of said probe, into said other of said patient's puncta, said other of said patient's canaliculi, said common canaliculus, said lacrimal sac and said DCR ostium into said nasal cavity;

reaching up said nasal cavity and grasping said probe and pulling said probe down said nasal cavity and out the external naris;

removing said probe from said distal segment; and pulling said distal segment further down the nasal cavity and out the external naris, thus pulling said moderate diameter segment through said one canaliculus, said one punctum, said other punctum, said other canaliculus, said common canaliculus, said lacrimal sac and said DCR ostium into the nasal cavity and pulling said very large diameter end segment from said nasal cavity through the DCR ostium into said lacrimal sac, thus positioning said very large diameter end segment and said moderate diameter segment to stent said DCR ostium with said central segment lying on the eye between said puncta and in said canaliculi.

10. A method of inserting a lacrimal stent in a patient's lacrimal system having a surgically formed ostium, said stent comprising a silicone rod having a distal segment having a lumen extending from its distal end, said method comprising;

inserting a semi-rigid sheath through one of the patient's puncta, one of the patient's canaliculi, the patient's common canaliculus, the patient's lacrimal sac and the patient's ostium into the patient's nasal cavity, said sheath having a distal end;

reaching up the patient's nose and pulling said sheath down the patient's nose until the distal end of said sheath is outside the patient's external naris;

threading said distal segment of said silicone rod into said distal end of said sheath; and pulling said sheath back up the nose and out said one of the canaliculi and said one puncta, bringing said distal segment of said silicone tube through said one of the canaliculi and said one of the puncta.

11. The method of claim 10, wherein a metal rod is inserted in said sheath prior to the insertion of said sheath through the patient's lacrimal system said metal rod being removed from said sheath prior to the threading of said distal segment.

12. A method of inserting a lacrimal stent in a patient's lacrimal system having a surgically formed ostium, said stent comprising a silicone rod having a distal segment having a lumen extending from its distal end, said method comprising:

inserting a semi-rigid sheath through one of the patient's puncta, one of the patient's canaliculi, the patient's common canaliculus, the patient's lacrimal sac and the patient's ostium into the patient's nasal cavity, said sheath having a distal end;

reaching up the patient's nose and pulling said sheath down the patient's nose until the distal end of said sheath is outside the patient's external naris;

swaging said distal segment onto a relatively thinner distal portion of a metal probe, said probe having a proximate end;

threading the proximate end of said probe through said sheath until said proximate end of said probe emerges from the proximate end of said sheath, pulling said proximate end of said probe to pull said distal segment into said sheath; and removing said sheath.

13. A method of inserting a lacrimal stent in a patient's lacrimal system, having a surgically formed ostium between the patient's lacrimal sac and nasal cavity, said stent apparatus comprising a silicone rod with proximate and distal ends, and including a very large diameter end segment which at all times during said insertion of said stent has an outer diameter which is larger than the largest diameter stent which can be pulled through the patient's canaliculi without damaging the canaliculi, a moderate diameter segment having an outer diameter smaller than said largest diameter, a relatively thin central segment between said very large diameter end segment and said moderate diameter segment, and a distal segment between the distal end of said silicone rod and an end of said moderate diameter segment, said distal segment having a lumen extending from said distal end of said silicone rod for a portion of the length of said distal segment, said method comprising:

swaging said distal segment on an end of a metal probe;

threading said probe through said lacrimal system to pull said distal segment of said stent through said ostium, lacrimal sac, the patient's common canaliculus, one of the patient's superior and inferior canaliculi, and one of the patient's superior and inferior puncta; and threading said probe through the other of the patient's superior and inferior puncta, the other of the patient's superior and inferior canaliculi, the common canaliculus, the lacrimal sac and the ostium into the patient's nasal cavity;

grasping said probe in said nasal cavity and pulling said probe out the patient's external naris;

removing said probe; and grasping said distal segment and pulling said silicone rod to bring said moderate diameter segment through said other punctum and canaliculus, the common canaliculus, the lacrimal sac and the ostium into the nasal cavity to position said moderate diameter segment in said ostium and to bring said very large diameter segment from the nasal cavity partly through said ostium and into said lacrimal sac, whereby said moderate diameter segment and very large diameter are positioned to stent the ostium without pulling said, very large diameter segment through said common, superior or inferior canaliculus.

14. The method of claim 13, wherein said central segment is positioned with a portion between said superior and inferior puncta.

15. A method of inserting a lacrimal stent in a patient's lacrimal system, said stent apparatus comprising an elongated soft silicone member with proximate and distal ends having a distal segment and a lumen formed in said distal segment and extending from the distal end of said member, said distal segment forming a sidewall of said lumen, said method comprising:

bending a portion of said distal segment including said lumen at a first point spaced from said distal end of said silicone member;

inserting a distal portion of a probe through the sidewall of said lumen in the direction of said distal end to a second point spaced from said distal end of said silicone member;

pushing said distal portion of said probe within said distal segment and said distal segment through a patient's lacrimal system from one of the patient's puncta into the patient's nasal cavity; and removing said probe from said distal segment as said distal end is grasped in the patient's nasal cavity and pulled down.

16. The method of claim 15, wherein said distal segment is grasped between said second point and said distal end of said silicone member.

\* \* \* \* \*

UNITED STATES PATENT AND TRADEMARK OFFICE
CERTIFICATE OF CORRECTION

PATENT NO.    : 6,238,364 B1
DATED         : May 29, 2001
INVENTOR(S)   : Bruce B. Becker It is certified that error appears in the above-identified patent and that said Letters Patent is hereby corrected as shown below:

<u>Title page,</u>
Item [75], Inventor's address, the ZIP code is changed to -- 91316 --.

Item [57], ABSTRACT,
Lines 8 and 10, "lumina" has been changed to -- lumen --.

<u>Column 1,</u>
Line 53, change "must" to -- much --.

<u>Column 6,</u>
Line 53, change "stem" to -- stent --.

<u>Column 7,</u>
Linr 56, insert -- diameter -- before "segments".

<u>Column 12,</u>
Line 63, change "rob" to -- rod --.

<u>Column 13,</u>
Line 39, before "inch" insert -- an outer diameter of 0.045 --.
Line 40, after "inch" insert -- and a --.

<u>Column 14,</u>
Line 60, change "puncta" to -- punctum --.

Signed and Sealed this

Eleventh Day of June, 2002

*Attest:*

*Attesting Officer*

JAMES E. ROGAN
*Director of the United States Patent and Trademark Office*